United States Patent
Bartee

(10) Patent No.: US 11,607,317 B2
(45) Date of Patent: Mar. 21, 2023

(54) MODELING DEVICES USED IN GUIDED BONE AND TISSUE REGENERATION

(71) Applicant: Osteogenics Biomedical, Inc., Lubbock, TX (US)

(72) Inventor: Barry K Bartee, Lubbock, TX (US)

(*) Notice: Subject to any disclaimer, the term of this patent is extended or adjusted under 35 U.S.C. 154(b) by 146 days.

(21) Appl. No.: 17/026,151

(22) Filed: Sep. 18, 2020

(65) Prior Publication Data

US 2021/0085471 A1    Mar. 25, 2021

Related U.S. Application Data

(60) Provisional application No. 62/902,898, filed on Sep. 19, 2019.

(51) Int. Cl.
*A61F 2/30* (2006.01)
*A61F 2/28* (2006.01)
(Continued)

(52) U.S. Cl.
CPC .......... *A61F 2/30942* (2013.01); *A61B 34/10* (2016.02); *A61F 2/2846* (2013.01); *A61L 27/18* (2013.01); *B33Y 50/02* (2014.12); *B33Y 80/00* (2014.12); *G05B 19/4099* (2013.01); *G05B 19/4155* (2013.01); *G06Q 50/04* (2013.01);
(Continued)

(58) Field of Classification Search
CPC ..... A61F 2/30942; A61F 2/2846; A61L 27/18
See application file for complete search history.

(56) References Cited

U.S. PATENT DOCUMENTS

| | | |
|---|---|---|
| 2015/0366669 A1 | 12/2015 | Bartee et al. |
| 2017/0281829 A1 | 10/2017 | Biris |
| 2017/0287212 A1 | 10/2017 | Tran et al. |
| 2017/0360565 A1 | 12/2017 | Seiler |

FOREIGN PATENT DOCUMENTS

| | | |
|---|---|---|
| EP | 0622052 A1 | 11/1994 |
| WO | 2009137947 A1 | 11/2009 |

(Continued)

OTHER PUBLICATIONS

PCT/US2020/051804. IInternational Preliminary Report on Patentability (dated Mar. 31, 2022). pp. 12.
(Continued)

*Primary Examiner* — Jason-Dennis N Stewart
(74) *Attorney, Agent, or Firm* — Loza & Loza, LLP; Anthony G. Smyth

(57) ABSTRACT

This disclosure describes manufacturing of a device configured to guide bone and tissue regeneration for a bone defect. A method may include receiving a three-dimensional digital model or scan representing an anatomical feature to be repaired, generating a simulated membrane using the three-dimensional model, the simulated membrane being configured to cover the anatomical feature to be repaired, generating a digital two-dimensional flattened version of the simulated membrane, and generating code or instructions configured to cause a three-dimensional printer or milling device to produce a trimming guide that includes an opening corresponding to the flattened version of the simulated membrane and that further includes a cut-out configured to hold a premanufactured membrane. The trimming guide may be operative as a guide for marking or cutting the premanufactured membrane through the opening while the premanufactured membrane is held in the cut-out.

25 Claims, 14 Drawing Sheets

(51) Int. Cl.
    *A61L 27/18*     (2006.01)
    *G06Q 50/04*     (2012.01)
    *G16H 50/50*     (2018.01)
    *G16H 30/40*     (2018.01)
    *G05B 19/4099*     (2006.01)
    *G05B 19/4155*     (2006.01)
    *B33Y 50/02*     (2015.01)
    *B33Y 80/00*     (2015.01)
    *A61B 34/10*     (2016.01)

(52) U.S. Cl.
    CPC ............. *G16H 30/40* (2018.01); *G16H 50/50* (2018.01); *A61B 2034/104* (2016.02); *A61B 2034/105* (2016.02); *A61B 2034/108* (2016.02); *A61F 2002/285* (2013.01); *A61F 2002/3096* (2013.01); *A61F 2002/30952* (2013.01); *A61F 2002/30963* (2013.01); *A61F 2002/30985* (2013.01); *A61L 2430/02* (2013.01); *G05B 2219/37355* (2013.01); *G05B 2219/49023* (2013.01)

(56) References Cited

FOREIGN PATENT DOCUMENTS

WO     WO2009137947 A1     11/2009
WO     2018059950 A1     4/2018

OTHER PUBLICATIONS

PCT/US2020/051804. International Search Report & Written Opinion (dated Mar. 11, 2012). pp. 17.
EP Application 20865143.0; Extended European Search Report and Written Opinion (EESR) dated Oct. 14, 2022. 8 pages.

MODELING DEVICES USED IN GUIDED BONE AND TISSUE REGENERATION

PRIORITY

This application claims priority to and the benefit of U.S. Provisional Patent Application Ser. No. 62/902,898 filed in the U.S. Patent Office on Sep. 19, 2019, the entire content of this application being incorporated herein by reference as if fully set forth below in its entirety and for all applicable purposes.

TECHNICAL FIELD

The present disclosure relates to manufacture, customization and use of a device configured to guide bone and tissue regeneration for a bone defect.

BACKGROUND

It is widely known that the occurrence of tooth loss in human dentition (which may happen as the result of dental diseases, advanced age, genetic inclination, accidents, etc.) is the cause of a number of functional and aesthetic problems. For example, if chewing is unsatisfactory, the entire digestive system may be affected, and the unsatisfactory chewing may cause gastrointestinal dysfunction and complaints. From an aesthetic point of view, properly cared for teeth have considerable significance.

Previously, missing teeth were replaced with a partial denture or a permanently attached dental bridge, supported in part by the remaining natural teeth. Bridges, however, are multi-piece inflexible systems, the shape and color of which do not always conform to expectations, and their participation in the chewing process is also frequently imperfect. Contemporary tooth replacement includes the extraction of damaged or hopeless teeth and implantation titanium implants supported by the patient's own natural bone. If there is inadequate bone for implant support, this bone may be reconstructed using autogenous bone grafts. This expensive procedure may require hospitalization and carries risks of complications. Other options for bone reconstruction include guided tissue regeneration (GTR) and bone regeneration (GBR). Both of these techniques involve the regeneration of bone deficiencies affecting natural teeth by means of barrier membranes. GTR implies the regeneration of the bone and attachment apparatus (ligaments, cementum) of natural teeth, whereas GBR includes the implantation of a membrane into the location where the formation of bone is intended. For either technique, bone and/or bone replacement material is typically used under the membrane.

There is an ongoing need for improved material and techniques for use in GTR and GBR procedures.

SUMMARY

Certain aspects of the disclosure relate the manufacture of a membrane configured to guide bone and tissue regeneration for a bone defect. The membrane may include a reinforced polytetrafluoroethylene (PTFE) mesh. A PTFE mesh may be referred to herein as a membrane. The membrane may comprise a first layer, a second layer, one or more perforations, a reinforcement binder, and/or other components. The first layer of the membrane may be configured to contact bone. This is not intended to be limiting. In some situations, a user may place the first layer of the membrane in contact with soft and/or other non-bone tissue. The second layer may be configured to substantially prevent fibrous connective tissue from growing into the bone defect. The reinforcement binder may be configured to be placed over the bone defect and coupled with surrounding bone. The reinforcement binder may comprise multiple elongated members extending from a junction. Certain aspects of the disclosure relate to membranes that are manufactured using modeling and/or simulation tools to design, configure, print and/or cut the membrane and/or materials used to make the membrane.

In one aspect of the disclosure, a method for manufacturing a device configured to guide bone and tissue regeneration includes receiving a three-dimensional model representing an anatomical feature to be repaired, generating a simulated membrane using the three-dimensional model, the simulated membrane being configured to cover the anatomical feature to be repaired, manufacturing the device to match physical structure of the simulated membrane, and drilling one or more holes in the device to be used for fixing the device to bone adjacent to the anatomical feature to be repaired. In one example, manufacturing the device includes cutting a premanufactured membrane according to a template corresponding to the simulated membrane. In one example, manufacturing the device includes printing at least one layer of material using template information derived from the simulated membrane, and joining the at least one layer of material to one or more other layers of material to obtain the device.

In one aspect of the disclosure, a device configured for repair of a bone defect comprises a first layer configured to contact bone, the first layer comprising expanded polytetrafluoroethylene (ePTFE), a second layer comprising high density, cell occlusive polytetrafluoroethylene (PTFE) configured to substantially prevent fibrous connective tissue from growing into the bone defect, and one or more holes drilled through the device and configured to receive fasteners for fixing the device to bone adjacent to the anatomical feature to be repaired. The device may be manufactured using template information generated from a three-dimensional model representing an anatomical feature to be repaired. In some examples, the device may be manufactured by cutting a premanufactured membrane according to the template information. In some examples, the device is manufactured from one or more layers of material printed using the template information, wherein the one or more layers of material are joined to obtain the device.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

Figure 1:
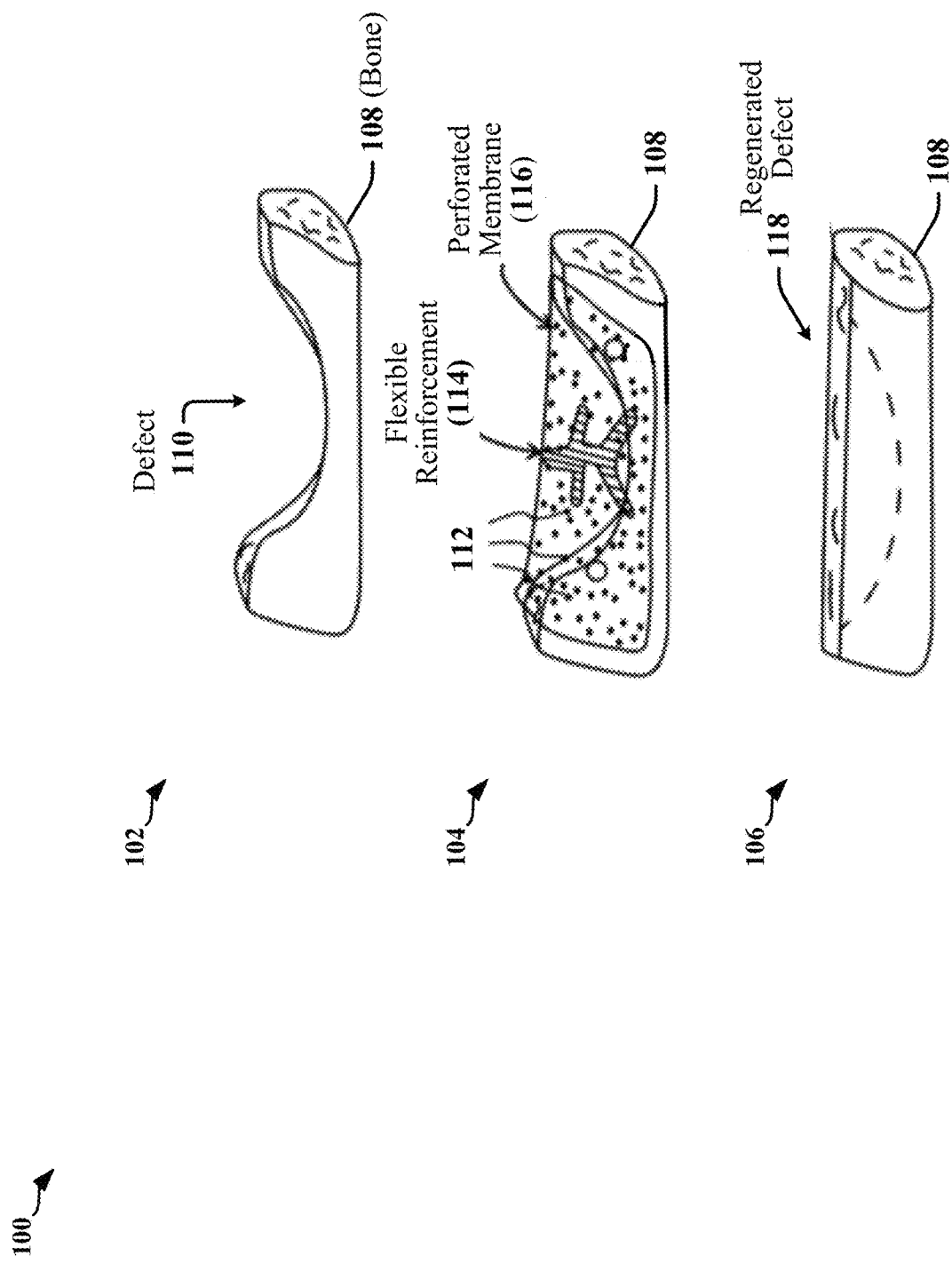
FIG. 1 illustrates treatment of a discontinuity defect with a membrane.

FIG. 1 illustrates a sequence 100 related to the treatment of a discontinuity defect 110 in a bone 108 using a device 116 that may be comprise or function as a membrane. The device may also be referred as a membrane. In one example, the sequence 100 may relate to procedure to a correct or repair an initial condition 102 to obtain a desired outcome 106 by inducing, assisting and/or enhancing bone regeneration 118 in the area of the discontinuity defect 110. Bone regeneration 118 may be accelerated using a device 116 provided in accordance with certain aspects of this disclosure. In some instances, the device 116 may be perforated to enhance ossification. In some implementations, the device may include a PTFE mesh.

The device 116 may have multiple layers, including a first layer that faces the discontinuity defect 110 and is fastened to the second, outward-facing layer. The first layer and/or the second layer may include perforations 112, and a reinforcement binder 114 may be attached to the device 116 in a manner that provides mechanical strength and/or enables the device to be fastened to areas of the bone 108 surrounding the discontinuity defect 110. During a bone regeneration phase 104, the device 116 may be placed across, over, and/or around the location of the discontinuity defect 110 and fastened in place at the location of the discontinuity defect 110 by screws, tacks, pins, and/or other fasteners.

The device 116 may be configured to guide bone and tissue regeneration for a variety of types of bone defects. The device 116 may be suitable for guided bone regeneration (GBR), guided tissue regeneration (GTR), and/or other therapies. The device 116 may form a barrier device used for guiding bone and tissue regeneration for dental and/or other purposes. The device 116 may be used in oral surgery, maxillofacial surgery, craniofacial surgery, to treat periodontal diseases, for dental implants, to treat orbital floor bone defects, and/or for other applications. The device 116 may be configured to maintain space for bone regeneration, to prevent connective tissue fibers from growing into the bone tissue, to immobilize bone, to exclude stimuli, which may hinder bone generation, and/or for other purposes. The device 116 may be a barrier device that is applicable in alveolar ridge defect replacements and/or for other defects that the device 116 is sized to cover. The device 116 may facilitate reducing and/or eliminating injuries, and/or facilitate a more efficient bone and tissue regeneration process compared to previously known techniques. The device 116 may include perforations 18 located at various distances from each other throughout the device 116.

Perforations 112 in the device 116 may be provided such that the barrier membrane does not constitute a continuous surface at the location of the desired bone and tissue regeneration. For example, a discontinuous surface may be presented when the device 116 includes perforations that are larger than a pore size in a surface of the device 116. The device 116 can induce a positive effect on bone regeneration when a discontinuous surface is presented, particularly when combined with the use of various biological growth factors. Perforated membranes have been shown to better facilitate bone regeneration than membranes without perforations. The perforated design disclosed herein facilitates handling, fixating, and/or shaping of the device 116 during application because the surgeon may more readily visualize, for example, pilot holes made specifically for the purpose of securing membrane fixation screws, pins or tacks.

A device 116 that includes or operates as a perforated membrane may facilitate communication between a patient's periosteum and growth factors used with GBR. The growth factors may include RhPDGF (Platelet Derived Growth Factor), RhBMP (Bone Morphogenetic Protein), and/or other growth factors. The perforations 112 may also facilitate communication between the periosteum and undifferentiated stem cells, especially in the presence of stimulative growth factors. Application of a non-perforated collagen (for example) membrane may reduce the regenerative potential of PDGF. If a surgeon (and/or other users) utilizes ground autogenous bone for bone generation, which makes the application of a membrane necessary, the "permeability" of a perforated membrane may make the development of a connection with the periosteal membrane possible using the PDGF technique.

Similarly, the device 116 may be used with RhBMP. Using the device 116 with RhBMP may allow a surgeon (and/or other users) to avoid using a titanium net/mesh (used for its permeability relative to a non-perforated membrane), for example. A titanium net/mesh may cause complications because it is sharp and difficult to handle. Such complications may include, for example, damaging the gum of a patient or difficult removal (taking as long as thirty minutes). Conversely, the device 116 may be removable in a matter of a few minutes, which decreases the duration of surgery and the possible occurrences of complications.

Continuing with the above non-limiting example comparison to the titanium net/mesh, the present invention differs from titanium mesh in several respects. These include mechanical compliance, placement, removal, customization, and/or other differences. (1) Mechanical Compliance: perforated PTFE is more flexible, and therefore has improved compliance with soft tissue compared to titanium mesh. Mechanical compliance is important because biomaterials that are compliant with soft tissue have a much less reduced risk of soft tissue dehiscence (opening) and/or wound healing complications. (2) Placement: because of its flexibility and softness, the device 116 may be easier to adapt, place, and/or fixate compared to titanium mesh. (3) Removal: regenerated bone tends to grow through and/or over the titanium mesh struts, making it exceedingly difficult to remove. During removal of titanium mesh, damage to the immature regenerated bone may occur, resulting in less volume of regenerated tissue than desired. In contrast, with the device 116 being flexible, it is much easier to remove and in fact is able to stretch and therefore presents less risk of damaging the newly formed bone tissue as the device is removed. (4) Customization: relating to method, in a 'custom fit' application, the present invention is much easier to trim and cut, and/or the surgeon may easily punch holes directly at the time of surgery with a simple hand punch, enabling the creation of a truly custom surgical device for individual defects. The surgeon may place the holes in exactly the location desired, and they may make more holes, or fewer holes depending on the clinical indication. For example, it may be advantageous in a case where membrane exposure was desired, to leave the exposed portion non-perforated and to create perforations in the areas where communication between the periosteum and graft bed was desired. This maneuver would be exceedingly difficult to accomplish with a sheet of titanium.

Figure 2:
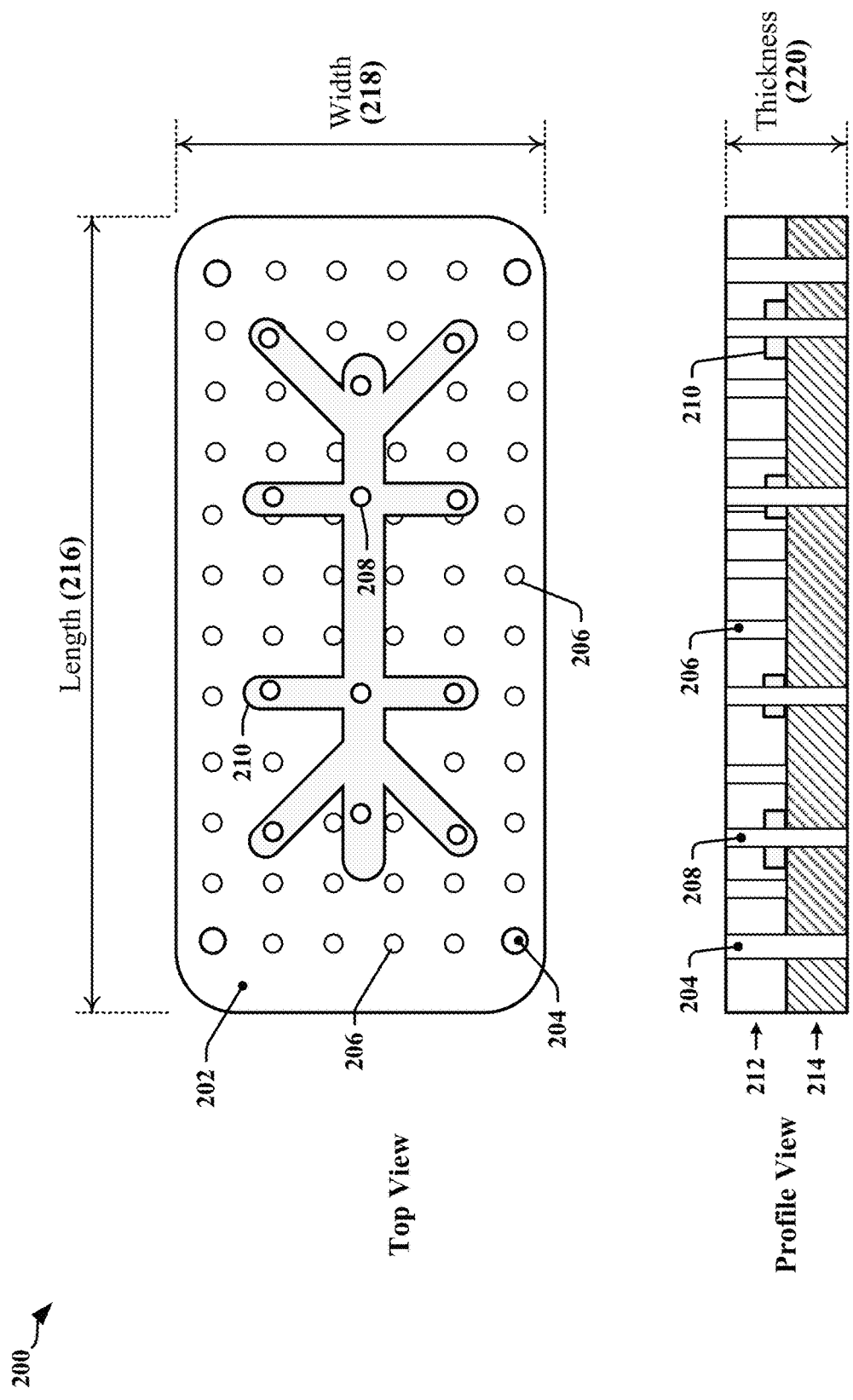
FIG. 2 illustrates a device that may be adapted or manufactured in accordance with certain aspects disclosed herein.

FIG. 2 illustrates a device 200 that may be adapted or manufactured in accordance with certain aspects disclosed herein. In some implementations, the device 200 may include a first layer 212, a second layer 214, one or more perforations 204, 206, 208, a reinforcement binder 210, and/or other components. In some implementations, the first layer 212 may be non-perforated, and consist of a thin layer of lightweight polymer mesh, collagen or expanded PTFE. Some perforations 206 may be completed through only a single layer of the device 200, with the layer of lightweight polymer mesh, collagen, or expanded PTFE bonded (for example) to the single layer. In some examples, the device 200 may include or incorporate a titanium framework between the layers 212, 214. In the illustrated example, the device 200 includes a reinforcement binder 210.

In the illustrated example, the device 200 may be generally rectangular and have a length 216 and a width 218. In one example, the length 216 may be less than about 50 mm. The length 216 may be between about 30 mm and about 50 mm. The length 216 may be about 40 mm. In some implementations, the width 218 may be less than about 40 mm. The width 218 may be between about 20 mm and about 40 mm. The width 218 may be about 30 mm. In some implementations, the device 200 may have a thickness 220 from about 0.125 mm to about 0.25 mm. The generally rectangular shape and approximate dimensions of the device 200 shown in FIG. 2 are not intended to be limiting. The device 200 may take any shape and have any dimensions that allow it to function as described in the present disclosure.

In some implementations, the device 200 may be formed from collagen, PTFE, and/or other materials, and/or a combination of materials. In some implementations, the device 200 made be formed from one or more of expanded PTFE, unsintered PTFE, high density PTFE, and/or other materials. In some implementations, one or more layers 212, 214 of the device 200 may be formed from unsintered substantially unexpanded PTFE. The term sintered is a term well known in the art and is used herein consistent with that understanding. The term unsintered is used herein to describe PTFE polymer that has not been subjected to the sintering process. Unsintered PTFE may be substantially unexpanded and typically contains no substantially defined internodal distance, which may substantially reduce its porosity relative to expanded PTFE. The limited porosity of the unsintered, substantially unexpanded PTFE may substantially reduce tissue adhesion to the unexpanded PTFE and/or migration of tissue into the unexpanded PTFE. However, the limited porosity may allow for the passage of ions and other small molecules necessary for cellular nourishment and waste transport. In some implementations, a density of one or more layers 212, 214 of the device 200 may be about 1.2 gm/cc to about 2.3 gm/cc. In some implementations, the density of one or more layers 212, 214 of the device 200 may be about 1.45 gm/cc to about 1.55 gm/cc.

Referring also to FIG. 1, a first layer 212 may be configured to contact bone 108. (This is not intended to be limiting. In some situations, a user may place the first layer of the device 200 in contact with soft and/or other non-bone tissue. For example, surgeons may choose to place the expanded PTFE layer or the dense PTFE layer towards bone, or soft tissue). The first layer 212 may have a surface 202 that includes pores or perforations 112 configured to promote ingrowth of bone regenerating cells into the first layer 212. A second layer 214 may be fixedly coupled to first layer 212 and/or be coupled to first layer 212 in other ways. The second layer 214 may be configured to substantially prevent fibrous connective tissue from growing into the bone defect. The second layer 214 may comprise a dense structure that prevents tissue ingrowth. The second layer 214 may be relatively denser than first layer 212, for example. The first layer 212 and the second layer 214 may be separate layers of the device 200 (as described above), and/or the first layer 212 and the second layer 214 may be two surfaces on opposite sides of the device 200 (e.g., opposite sides of a single layer).

The pores in materials used to construct the first layer 212 and/or the second layer 214 may be formed during manufacture of the materials. Pores may be formed due to the presence of expanded gases, material deformations and other cause during manufacture. For example, pores may be formed as a cavity in a material forming a layer 212, 214 of the device 200. The pores may be caused during manufacture when gases in the material expand to form a bubble. In one example, pores may be formed in expanded polytetrafluoroethylene (ePTFE), and the pores may range in size from 30 microns to 500 microns. Processes employed in the manufacture of an ePTFE material may be adapted to cause formation of pores of a desired size and distribution throughout at least a portion of the ePTFE material. The pores in the ePTFE material may be configured to promote ingrowth of bone regenerating cells into the first layer. Other layers may comprise a high density, cell occlusive PTFE configured to substantially prevent fibrous connective tissue from growing into the bone defect. In some instances, the cell occlusive PTFE has a dense structure. The cell occlusive PTFE may be fixedly coupled to the ePTFE layer.

Figure 3:
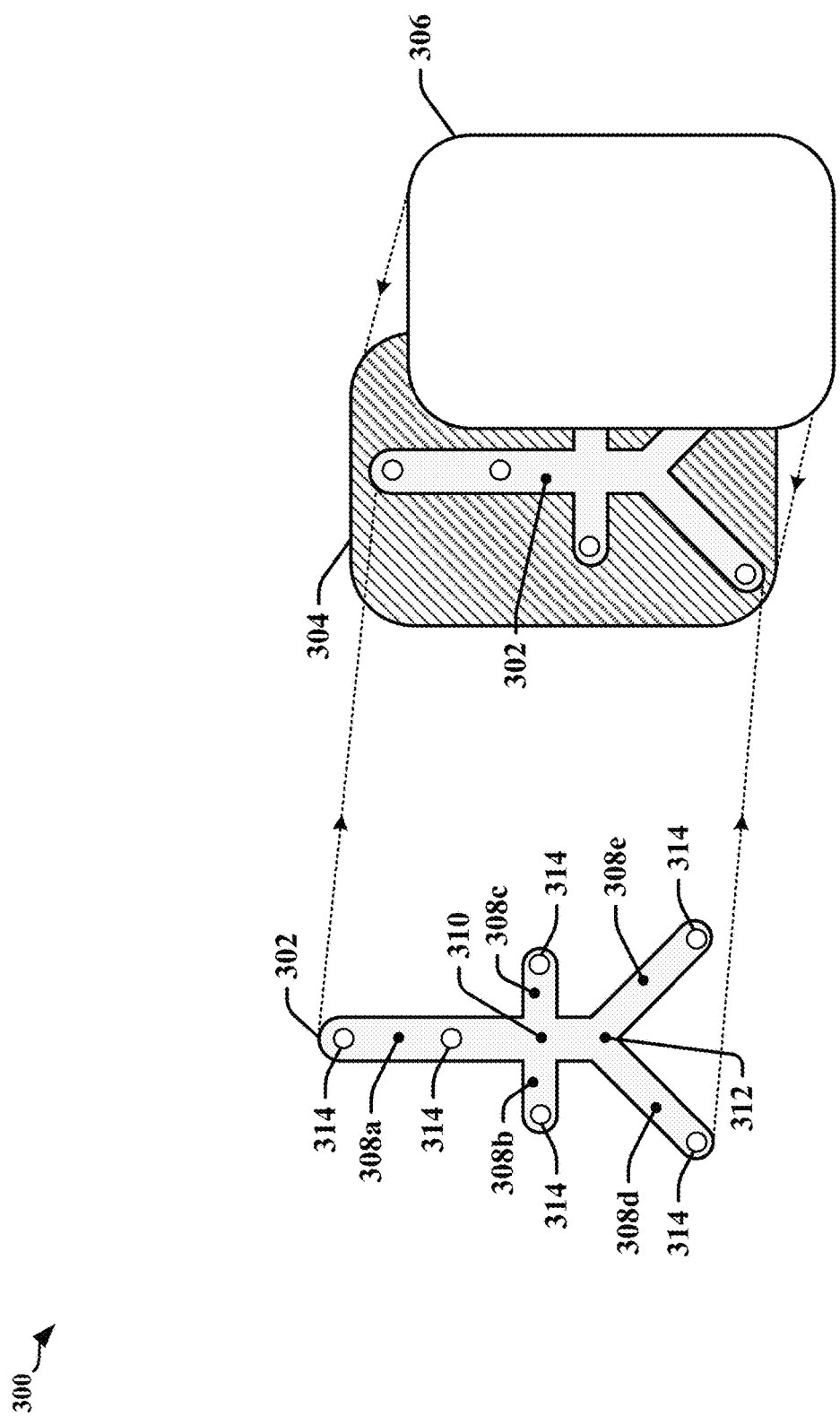
FIG. 3 illustrates an example of manufacture of a device provided in accordance with certain aspect disclosed herein.

FIG. 3 is an assembly drawing that illustrates the certain aspects of manufacture and/or construction of a device 300 provided in accordance with certain aspect disclosed herein. The illustrated device 300 has a reinforcement binder 302 that is provided between two layers 304, 306. By way of a non-limiting example, the first layer 304 may be constructed from ePTFE or may include ePTFE. The second layer 306 may be constructed from unsintered high density PTFE (d-PTFE) or may include d-PTFE. In one example, the d-PTFE gas a density of about 1.2 gm/cc to about 2.3 gm/cc. In some implementations, the density of d-PTFE may be in a range from about 1.45 grams/cc to about 1.55 grams/cc. The d-PTFE material may be unsintered and unexpanded with a nominal pore channel size of less than about 5 micrometers. In some implementations, the unsintered, unexpanded d-PTFE may have a nominal pore channel size of less than about 2 micrometers. In some implementations, the unsintered, unexpanded d-PTFE may have a nominal pore channel size of less than about 0.5 micrometers. In some implementations, the unsintered, unexpanded d-PTFE may have a nominal pore channel size of less than about 0.2 micrometers. This small pore channel size may allow a composite multi-layer material employing d-PTFE to exhibit superior functional characteristics, resulting clinically in reduced host response (inflammation), soft tissue in-growth, and resultant adhesions. (These pore channel sizes may be smaller than pore sizes in the first layer 304 made from ePTFE that promote bone ingrowth.)

The reinforcement binder 302 may include multiple elongated members 308a-308e. In the illustrated example, a primary elongated member is coupled to a pair of elongated members 308b, 308c that extend from a first junction 310, and to a pair of elongated members 308d, 308e that extend from a second junction 312. In some implementations the reinforcement binder 302 may be formed from titanium, stainless steel, platinum, ceramics, composites, carbon fiber materials, customized micro and/or nano material based materials, coated (e.g., with a non-toxic coating) materials, and/or other materials. The reinforcement binder 302 may be bendable and may include elongate members 308a-308e such that the reinforcement binder 302 may be formed in a desired shape (e.g. at manufacture), and/or may be bent, deformed, and/or reformed by a user to obtain the desired shape prior to placement about the bone defect such that the formed shape is maintained upon placement. For example, one or more portions and/or all of the reinforcement binder 302 may be bent, twisted, and/or stretched as necessary to obtain the desired shape. In some implementations, the reinforcement binder 302 may be malleable and/or flexible because it is relatively thin. For example, a thin piece of titanium may be easily bent by a user.

The reinforcement binder 302 may be placed over a bone cavity, such as an alveolar cavity, for example. One or more of the elongated members 308a-308e may have at least one predrilled hole 314 formed therein. The pre-drilled holes 314 may be suitable for receiving and/or positioning a fastener such as a surgical pin or screw at the bone defect site. In the illustrated example, two elongate members 308d and 308e are provided in a Y-shaped configuration, both elongate members 308d and 308e having a pre-drilled hole 314 for receiving a fastener. The fastener may be a surgical screw, for example, configured to fasten the corresponding elongate member 308d, 308e to an area of bone, typically at a surgical site, including on the buccal side of the jaw, or upper alveolar arch, in the repair of alveolar defects and/or maxillofacial defects, for example.

The two layers 304, 306 may be coupled with reinforcement binder 302 by fixing, attaching, and/or otherwise joining the layers and reinforcement binder 302 together. The two layers 304, 306 and the reinforcement binder 302 may be coupled using any suitable means, including use of an adhesive layer for attachment and/or bonding the two layers 304, 306 and the reinforcement binder 302. The two layers 304, 306 may partially cover the reinforcement binder 302. The two layers 304, 306 may substantially envelope reinforcement binder 302.

Dimensions of reinforcement binder 302 may be selected based on the application (e.g., based on the bone defect to be treated). Similarly, the physical and mechanical properties of reinforcement binder 302 may be selected according to application. Titanium is used as the primary example herein. Surgical grade titanium may be used to provide malleability, strength, and low weight. It should be appreciated that titanium possesses strength and weight characteristics that, together with the biologically inert nature of the metal, offers advantages in many applications. It is contemplated that some applications may dictate that other dimensions, ratios of dimensions, and/or materials may be employed. For example, repair of bone material in a pelvis and/or a hip may require the use of steel and/or other materials.

The structural configuration of reinforcement binder 302 may be selected to facilitate ease of placement and/or use in reconstructive repair of bone defects of various sizes, related soft tissue repair, and/or skeletal surgery, for example. The structural configuration of reinforcement binder 302 may be selected to provide one or more appendages and/or elongate members suitable for placement about bone and/or surrounding tissue. The overall shape of reinforcement binder 302 may be selected to achieve a desired strength, load distribution, membrane support, placement of fasteners, comfort, ease of insertion and/or removal, and/or achieve other effects.

A texture pattern that may be formed in one or more of the layers 304, 306. The texture pattern may include a plurality of indentations formed in a layer 304, 306. The indentations may have any shape that allows a membrane to function as described herein. In some instances, the indentations are hexagonal in shape, although other shapes are contemplated and fall within the scope of this disclosure. The indentations may have a depth less than the thickness of the layer 304, 306 in which they are formed. In some implementations, the indentations may be up to about 0.15 mm deep and up to about 0.5 mm wide, for example. The indentations may be dimensioned based on the intended use for the membrane and/or on other factors. The distribution of indentations may be substantially uniform over a layer 304, 306, may vary systematically across the layer 304, 306, may be randomly distributed across the layer 304, 306, and/or have other distributions. For example, up to about 150 indentations may be provided per square centimeter over one of the layers 304, 306. As another example, up to about 250 indentations may be provided per square centimeter over one of the layers 304, 306.

Figure 4:
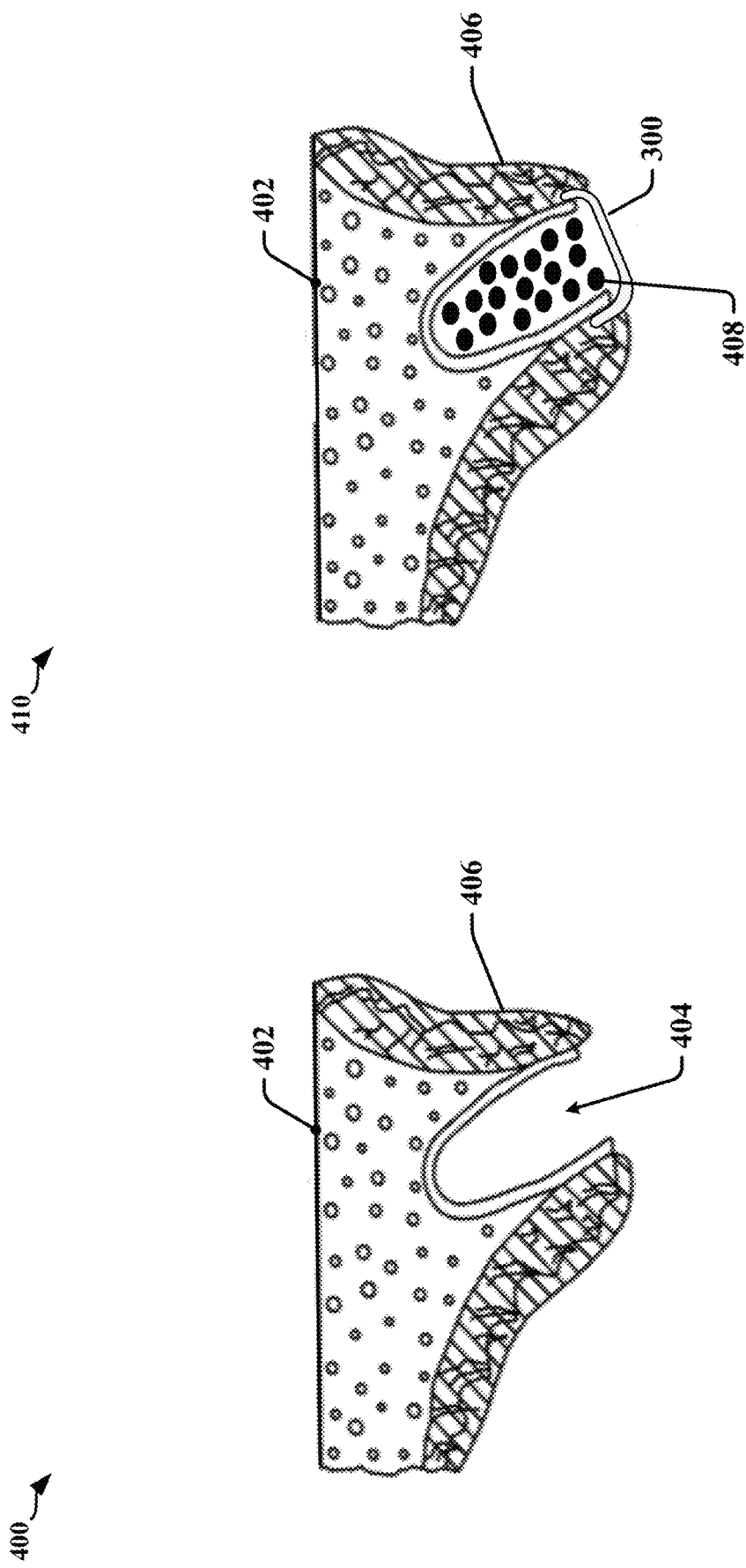
FIG. 4 illustrates the use of the device at a bone defect.

A texture pattern may be made by forming a thin sheet of PTFE and then embossing the sheet with indentations. PTFE resin may be mixed with a lubricant (e.g., mineral spirits) to form a paste. The paste may be calendered between rollers to form a thin flat sheet of the desired thickness (e.g., in the range of about 0.125 mm to about 0.25 mm.) The calendering may be performed to reduce the thickness of the sheet and to impart substantially uniform strength in all directions to the sheet. The lubricant may be removed by drying the sheet at a temperature somewhat above the boiling point of the mineral spirit lubricant, but well below the sintering temperature of PTFE. After the sheet has been dried, the sheet may be embossed to form the indentations in one of its surfaces. In some implementations, the embossing step may be performed by placing a sheet of patterned polymer mesh on top of the sheet of PTFE. The patterned polymer mesh may be harder and have more compressive strength than the PTFE material FIG. 4 illustrates the use of the device 300 at a bone defect. A first lateral cross-sectional view 400 relates to an adult human maxilla after a tooth extraction shows alveolar bone 402. Soft tissue gingiva 406 covers the bone 402. A tooth socket 404 provides an example of a bone defect. Normal healing of a defect may include migration of cells such as fibroblasts and gingival epithelial cells, for example. As the cells proliferate into the defect (here, the tooth socket 404), they may inhibit bone cell regeneration, which may result in overall loss of bone mass. In the case of extractions, the loss of bone mass may result in a loss of the alveolar ridge profile.

A second lateral cross-sectional view 410 shows the socket 404 packed with bone 408 and covered with the device 300. The socket 404 may be packed with granular particles of allograft, xenograft and/or bioresorbable hydroxyapatite, for example, as a precursor to bone, and/or other materials. Other materials and/or articles, such as endosseous type dental implants, may be placed into the socket 404. The packed socket 404 may be covered with the device 300. In one example, the device 300 may be secured in place via fasteners (not shown) after the device 300 is placed over the socket 404 and bone 402. Gingival flaps 406 may be sutured over the device 300. The device 300 may hold the hydroxyapatite particles and/or other materials in place in socket 404 during healing, and may prevent migration of cells and/or connective tissue into the socket 404. Connective tissue (e.g., gingival tissue 406) may form a weak attachment with the textured surface of the device 300, without growing through the device 300. The attachment may be weak enough that the device 300 may be removed after healing without significant trauma but may be strong enough to prevent dehiscence.

Certain aspects of this disclosure relate to the design, configuration and manufacture of devices or membranes used for guided bone and tissue regeneration. In some examples, a device or membrane includes a reinforced perforated PTFE mesh. Visualization or modeling systems may be used in preparations for surgical procedures related to guided bone and tissue regeneration treatment. Imaging technology can produce high-resolution three-dimensional (3D) renditions of physical structures and locations that may be a subject, target or candidate for guided bone and tissue regeneration treatment. For example, cone beam computed tomography (CBCT) can produce a series of high-resolution images used for diagnostic purposes and/or in preparation for dental implant procedures, orthopedic surgical procedures, and in other medical and dental fields. In one example, a CBCT scanner may produce hundreds of images captured from different perspectives around a location or feature of interest. A 3D image may be created by analyzing, combining and/or correlating information obtained from the images produced by the CBCT scanner. 3D images may be used to generate a model of a location of feature or interest. In one example, the model may combine image and dimension information.

Figure 5:
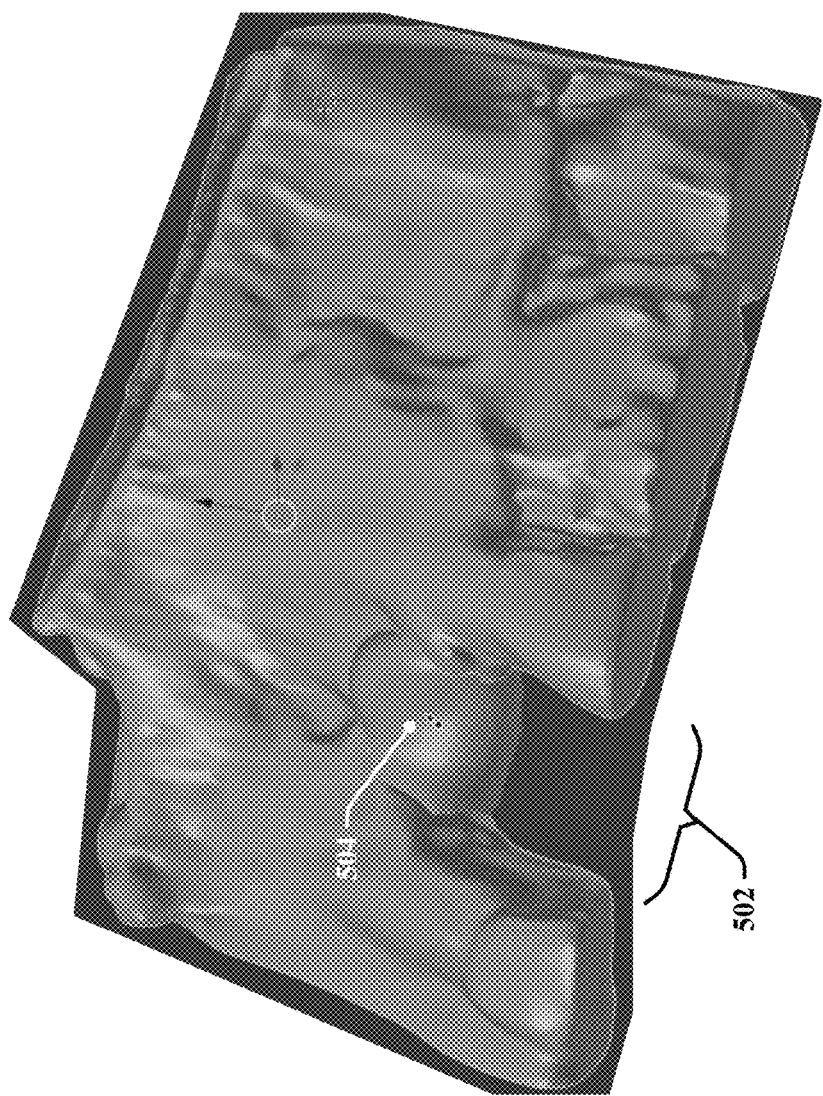
FIG. 5 illustrates a model of an adult human maxilla that includes a defect to be treated using guided bone and tissue regeneration.

A model generated by a 3D modeling system can be used by a simulation system. Certain 3D modeling systems may be configurable to use the model for one or more functions including simulation, animation, editing, rendering, and other functions. The model may be generated by any suitable commercial, proprietary or public domain 3D modeling system that is known in the art. The 3D modeling system may be used to generate a model of a location in preparation for a surgical procedure related to guided bone and tissue regeneration treatment. FIG. 5 is a two-dimensional view of a 3D model 500 of an adult human maxilla that includes a defect 502 to be treated using guided bone and tissue regeneration. The illustrated 3D model 500 has been modified to simulate the effect of adding packing material 504 to effectuate repair of the defect 502. The simulated packing material 504 may mimic the characteristics and attributes of granular particles of allograft, xenograft and/or bioresorbable hydroxyapatite, for example. The simulation represented by the 3D model 500 may be used to calculate the volume and shape of a packing material to be applied to repair the defect 502.

Figure 6:
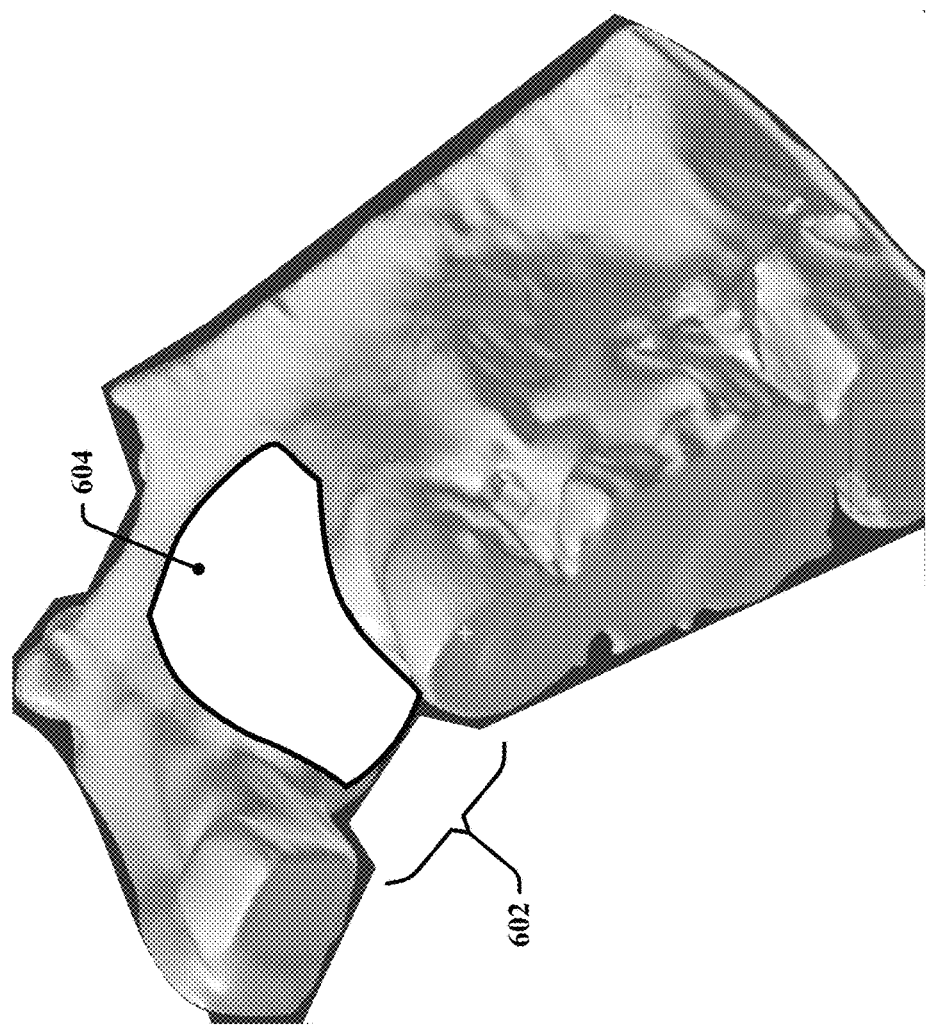
FIG. 6 illustrates a model used for planning a surgical procedure or preparing materials for the surgical procedure related to guided bone and tissue regeneration treatment.

Certain aspects of the disclosure relate to systems, apparatus and methods that can select, configure and/or modify a membrane or components of a membrane used to promote and support guided bone and tissue regeneration. FIG. 6 is a two-dimensional view of a 3D model 600 used for planning and/or preparing materials for a surgical procedure related to guided bone and tissue regeneration treatment. The 3D model 600 relates to an adult human maxilla, and has been modified to simulate the effect of adding packing material to effectuate repair of a defect 602. The 3D model 600 has been further modified to locate a simulated membrane 604 over the packing material in a manner that permits the simulated membrane 604 to be fastened to identifiable locations on the maxilla.

The size, location, orientation and shape of the simulated membrane 604 can be optimized based on the structure of the maxilla, the nature and location of the defect, the type and volume of the packing material and other characteristics, including the mechanical properties of the finished device or constituents of the finished device as represented by the simulated membrane 604. The size, location, orientation and shape of the simulated membrane 604 can be calculated using curve-fitting algorithms, including smoothing and/or interpolation algorithms for example. In some instances, the characteristics of the simulated membrane 604 may be used to adjust or optimize the structure, shape and/or volume of the packing material to be used. The simulated membrane 604 may be configured to meet design goals for maximum stress in the materials of the simulated membrane 604 and maximum and/or minimum pressures exerted on the packing material.

Other aspects of the simulated membrane 604 may be customized for the procedure to be performed. In one example, a surface of the simulated membrane 604 may be embossed with a pattern selected based on the type, size and composition of the packing material. The pattern may be selected based on area of the surface to be embossed, the area of contact between the simulated membrane 604 and packing material and/or bone or tissues, and other aspects of the procedure to be performed. In some instances, the pattern may be selected based on the physical structure and/or chemical composition of the simulated membrane 604. In another example, the location of holes that receive fasteners such as surgical pins or screws to the bone defect site may be calculated for drilling a reinforcement binder.

In some implementations, the design of the simulated membrane 604, including a reinforcement binder, may be expressed in one or more templates. The templates may be represented by information exchanged between different functional elements of a manufacturing system, including visualizers, modelers, 3D printers, cutting devices, drilling devices, bonding/welding devices, and other devices. In some instances, template information may be used to create a physical template.

Templates or template information may be used to customize pre-manufactured devices to fit the shape of the simulated membrane 604. The templates may include a drilling template that defines hole locations in the simulated membrane 604 and/or the reinforcement binder. A modeling system may be configured to generate a 3D model of the simulated membrane 604, and to produce a template from a flattened version of the simulated membrane 604. The modeling system may identify a premanufactured and/or commercially available membrane that can be modified to match the simulated membrane 604. The template can be used to cut the device to size and/or to drill holes in the device and/or reinforcement binder. A premanufactured and/or commercially available membrane may be selected from a catalog or other listing of available membranes based on fit, structure, mechanical strengths, shape and location information generated by a modeling system.

In some implementations, the design of the simulated membrane 604, including the reinforcement binder may be expressed in code used to control manufacturing machinery that can produce a device that matches the simulated membrane 604. In one example, the code may be used to control a 3D printer that can print one or more layers of the finished device. In another example, the code may be used to control a cutting machine that can modify the shape of a premanufactured and/or commercially available membrane. In another example, the code may be used to control a cutting machine that can cut binder material to form the reinforcement binder designed for the simulated membrane 604. In some instances, Laser or water jet cutters may be used. In another example, the code may be used to control a drilling machine that can drill a device to match defined holes in the simulated membrane 604 or the reinforcement binder.

Figure 7:
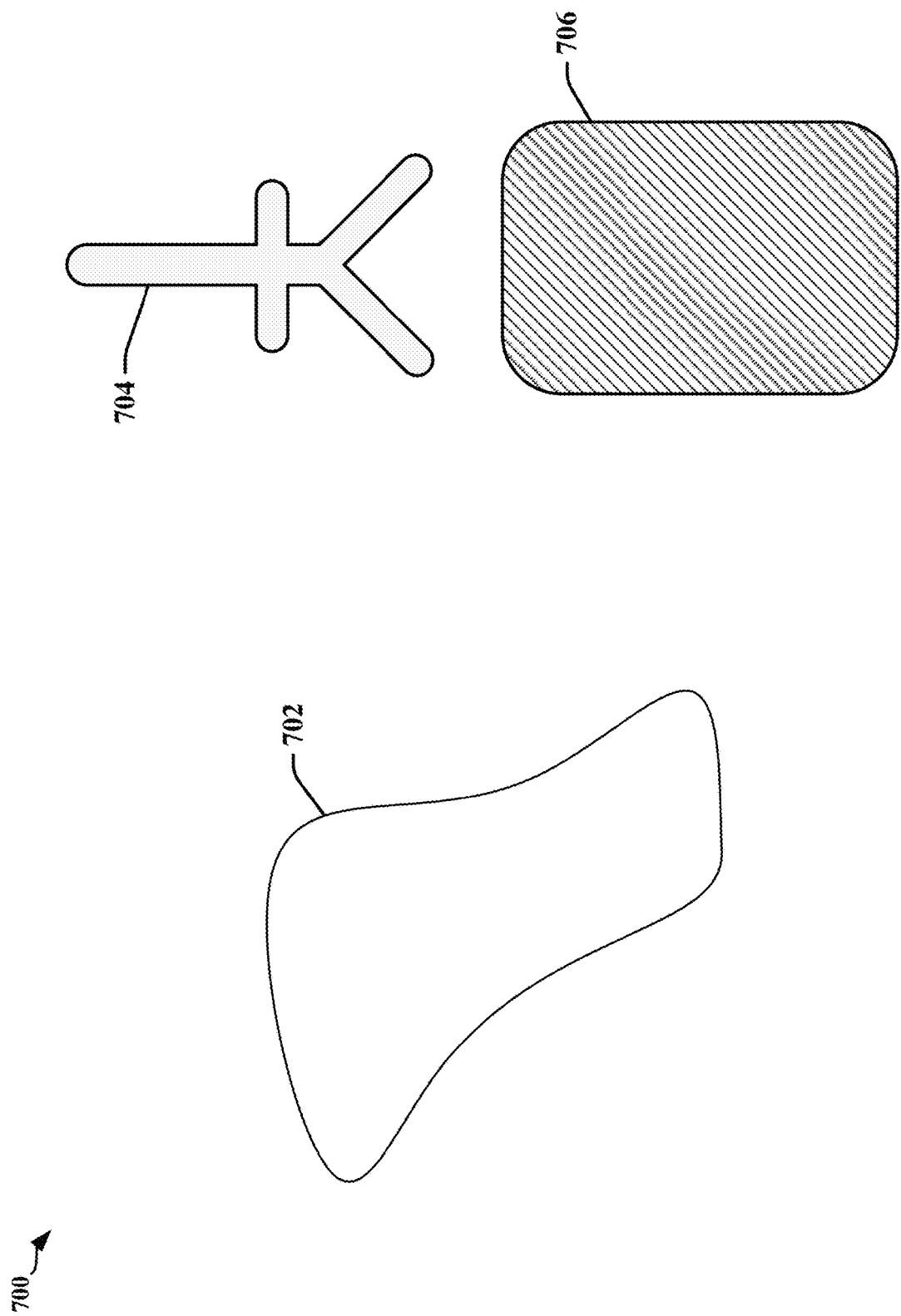
FIG. 7 illustrates an example of materials that may be used to create a device in accordance with certain aspects disclosed herein.

FIG. 7 illustrates an example of materials 700 that may be used to create a device corresponding to the simulated membrane 604 illustrated in FIG. 6. A two-dimensional template 702 may be generated from the 3D rendition of the simulated membrane 604. In some instances, a modeling system may identify a pre-manufactured membrane 706 that may be cut to fit the shape of the simulated membrane 604, and/or a reinforcement binder 704 that can be used to secure or strengthen the finished device. The template 702 may be used as an outline to customize the shape of the finished device.

Figure 8:
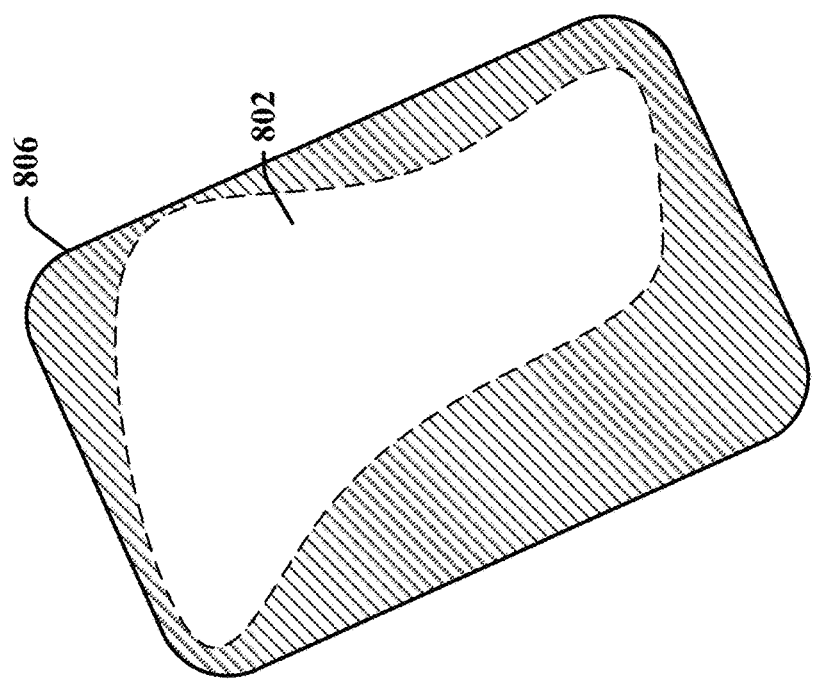
FIG. 8 illustrates a first example of a partially completed device conforming to the design of a simulated device provided in accordance with certain aspects disclosed herein.
Figure 8:
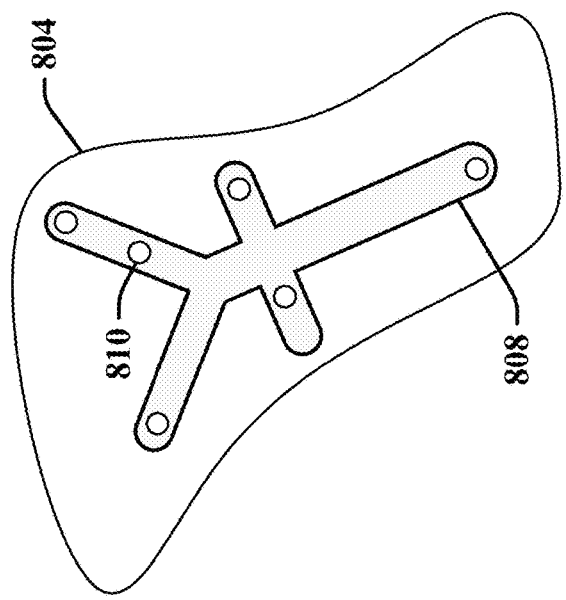

FIG. 8 illustrates a first example of a partially-completed membrane 800 conforming to the design of the simulated membrane 604. A first layer 804 has been cut using a template 802 and a reinforcement binder 808 has been drilled and positioned on a surface of the first layer 804. The reinforcement binder 808 may have been drilled according to a drilling template or program defined for the simulated membrane 604. One or more holes 810 may be provided in the reinforcement binder 808. In some instances, the holes 810 may supplement preexisting holes. In the illustrated example, the template 802 is used to mark and/or guide cutting of the second layer 806.

Figure 9:
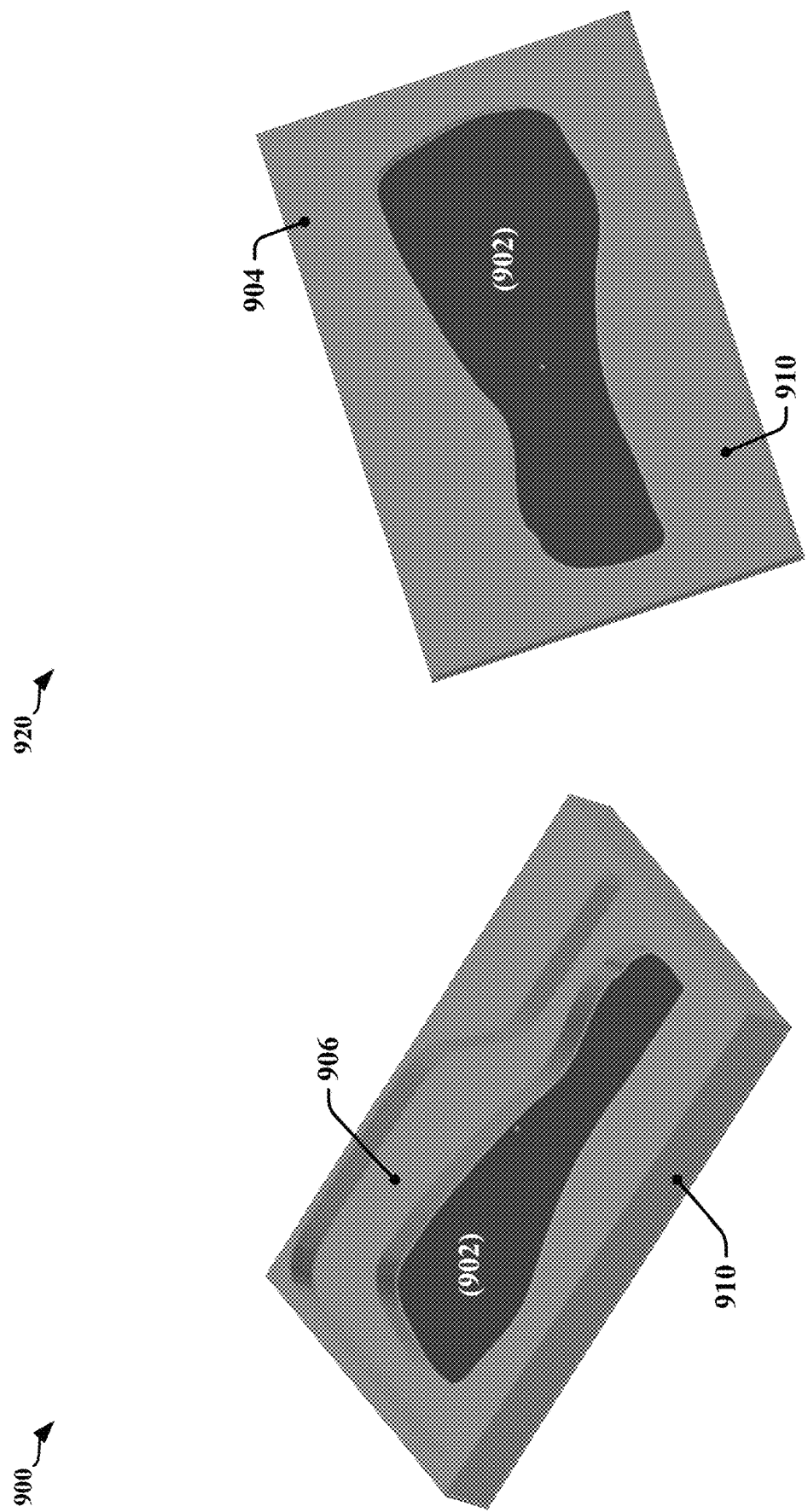
FIGS. 9 and 10 illustrate the use of a cutting guide produced using a three-dimensional model in accordance with certain aspects disclosed herein.

FIG. 9 illustrates an example of a trimming guide 910 generated in accordance with certain aspects disclosed herein. A top side 900 and a bottom side 920 of the trimming guide 910 are shown. The trimming guide 910 may be produced using a 3D model of a site that is the subject or target for a surgical procedure related to guided bone and tissue regeneration treatment. The trimming guide 910 may be generated to fit a simulated membrane designed by or developed from the 3D model of a surgical site, and/or designed by or developed during a simulation of the surgical procedure that is based on the 3D model of a surgical site. In one example, the trimming guide 910 may be 3D printed from sterilizable acrylic resin, or from some other suitable material. In other examples, the trimming guide 910 may be manufactured using numerically controlled equipment that cuts, routs or erodes a suitable block or sheet of material to form the trimming guide 910. In some instances, Laser or water jet cutters may be used.

A modeling system may be configured to generate a 3D model of a simulated membrane 604. The 3D model may be further used in the simulation of a surgical procedure. In some instances, the simulated membrane 604 may be further developed or modified during the surgical procedure. The trimming guide 910 may be generated, modified or developed from a flattened version of the simulated membrane 604. The modeling system may analyze a 3D model or simulation of the membrane and may flatten the 3D simulated or modeled membrane to produce a 2-dimensional (2D) rendition of the simulated or modeled membrane. In some implementations, the 2D rendition of the simulated membrane 604 can be printed for use as a cutting template or trimming guide 910. A membrane cut or trimmed to match the 2D rendition of the simulated membrane 910 can take the shape of the 3D simulated or modeled membrane when placed on the site targeted for surgery. In one example, the site targeted for surgery may be located on the jaw of a patient and the membrane cut to match the 2D rendition of the simulated membrane 910 can be curved over the jaw, substantially acquiring the shape of the 3D simulated or modeled membrane.

In one aspect, the modeling system may be configured to select a stock membrane that offers a best fit or best match to the flattened version of the simulated membrane 604. The stock membrane may be an untrimmed, commercially produced or commercially available prefabricated membrane. The stock membrane may be selected from a catalog or listing of prefabricated membranes based on size, shape and/or orientation information provided by the 3D modeling system. The 3D modeling system may produce information, including code and dimensional information that characterizes the size and shape of the 2D rendition of the simulated membrane 604 generated from a 3D model of the surgical site. The information may be used to create a 3D printed trimming guide 910 that includes an opening 902 on one surface that matches the size and shape of the 2D rendition of the simulated membrane 604. The 3D modeling system may identify a suitably or optimally sized commercially produced prefabricated membrane that may be trimmed to fit the size and shape of the 2D rendition of the simulated membrane 604. In some implementations, the 3D modeling system may be configured with a listing of specifications for commercially available prefabricated membranes and may select one or more candidates to serve as the base or starting membrane to be cut or trimmed using the trimming guide 910. In some implementations, the 3D modeling system may produce information that can be used by other equipment to select a suitably or optimally sized commercially produced prefabricated membrane and/or to print the trimming guide 910.

In the illustrated example, the top side 900 of the trimming guide 910 may include a cut-out section 906 configured to receive and hold the selected commercially produced prefabricated membrane. The trimming guide 910 may include the opening 902 in a bottom side 920 of the trimming guide 910, where the opening 902 conforms to the shape and size of the 2D rendition of the simulated membrane 604. A practitioner or technician may place an example of the commercially produced prefabricated membrane in the cut-out section 906. The practitioner or technician may cut, trim or mark the commercially produced prefabricated membrane through the opening 902 in the bottom side 920 of the trimming guide 910 thereby allowing for precise shaping of the membrane. In some instances, a prefabricated membrane can be cut or trimmed while held in place by the trimming guide 910. In some instances, the prefabricated membrane can be held in place by the trimming guide 910 while being marked using a surgical marker or scalpel, and the prefabricated membrane can be removed from the trimming guide 910 for final trimming.

The use of 3D modeling as disclosed herein can produce a properly trimmed membrane that fits the digitally created model derived from a cone beam scan, for example. The resultant trimmed membrane can be expected to fit the surgical site such that a surgeon is not required to further trim the membrane in a freehand manner in the operating room. Conventional techniques rely on shaping of the membrane by trial and error, whereby the surgeon trims the prefabricated membrane a little, trying it in situ, trimming some more, trying it in situ, until a fit was achieved.

Figure 10:
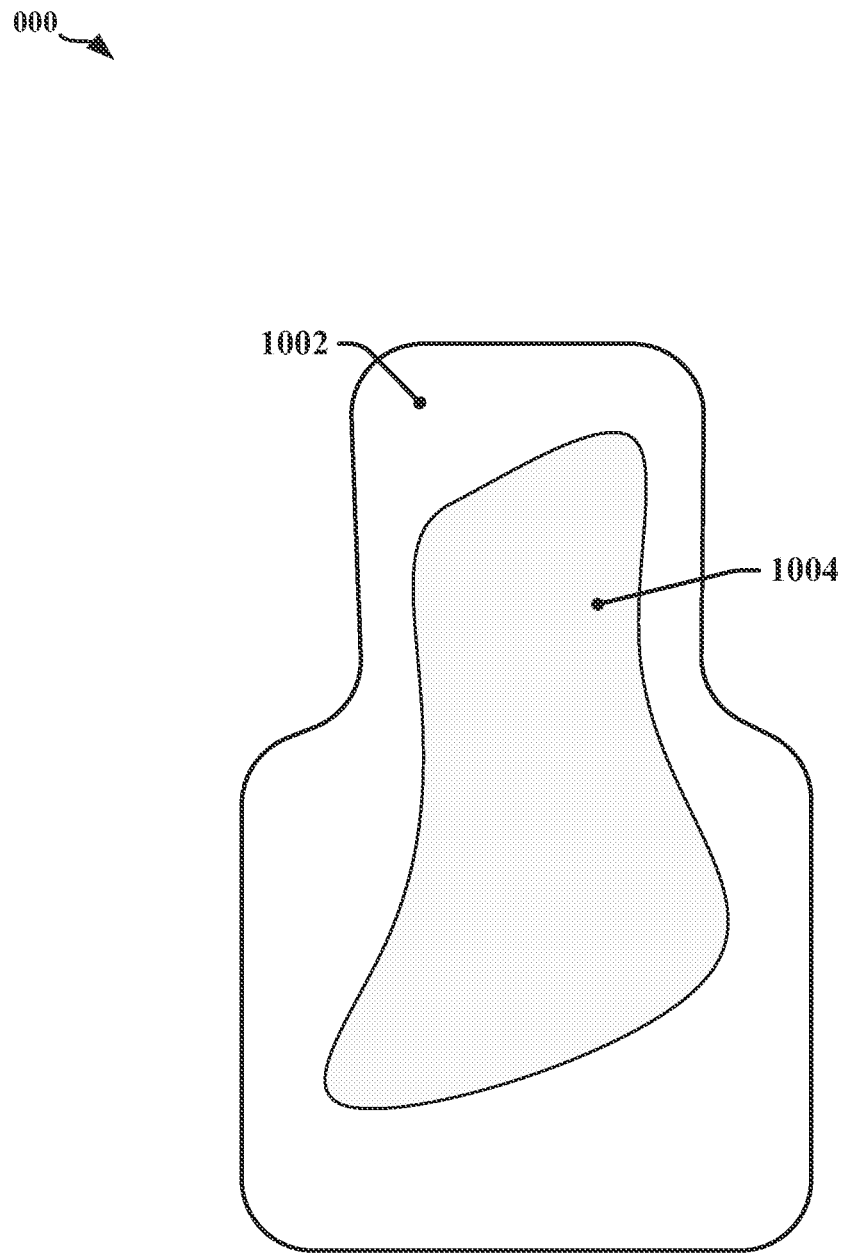

FIG. 10 illustrates an overlay 1000 of a shape 1004 corresponding to a 2D rendition of the simulated membrane 604 over a prefabricated membrane 1002. In one example, the overlay 1000 may represent the placement of the opening 902 in the trimming guide 910 illustrated in FIG. 9. In another example, the shape 1004 may represent an area of the surface of the prefabricated membrane 1002 created by marking the prefabricated membrane 1002 while it is held in the trimming guide 910. A 3D modeling operated in accordance with this disclosure can identify the prefabricated membrane 1002, and can define the shape, size and orientation of the shape 1004 within the trimming guide 910.

In some instances, a surgeon may choose to print the shape 1004 on paper or other material that can be used as a template to select a membrane or portion of a membrane that can accommodate the size, shape and, in some instance, orientation of the simulated membrane 604. For example, the surgeon may choose a best fit from among the pre-trimmed membranes identified in a catalog, with an idealized shape.

Figure 11:
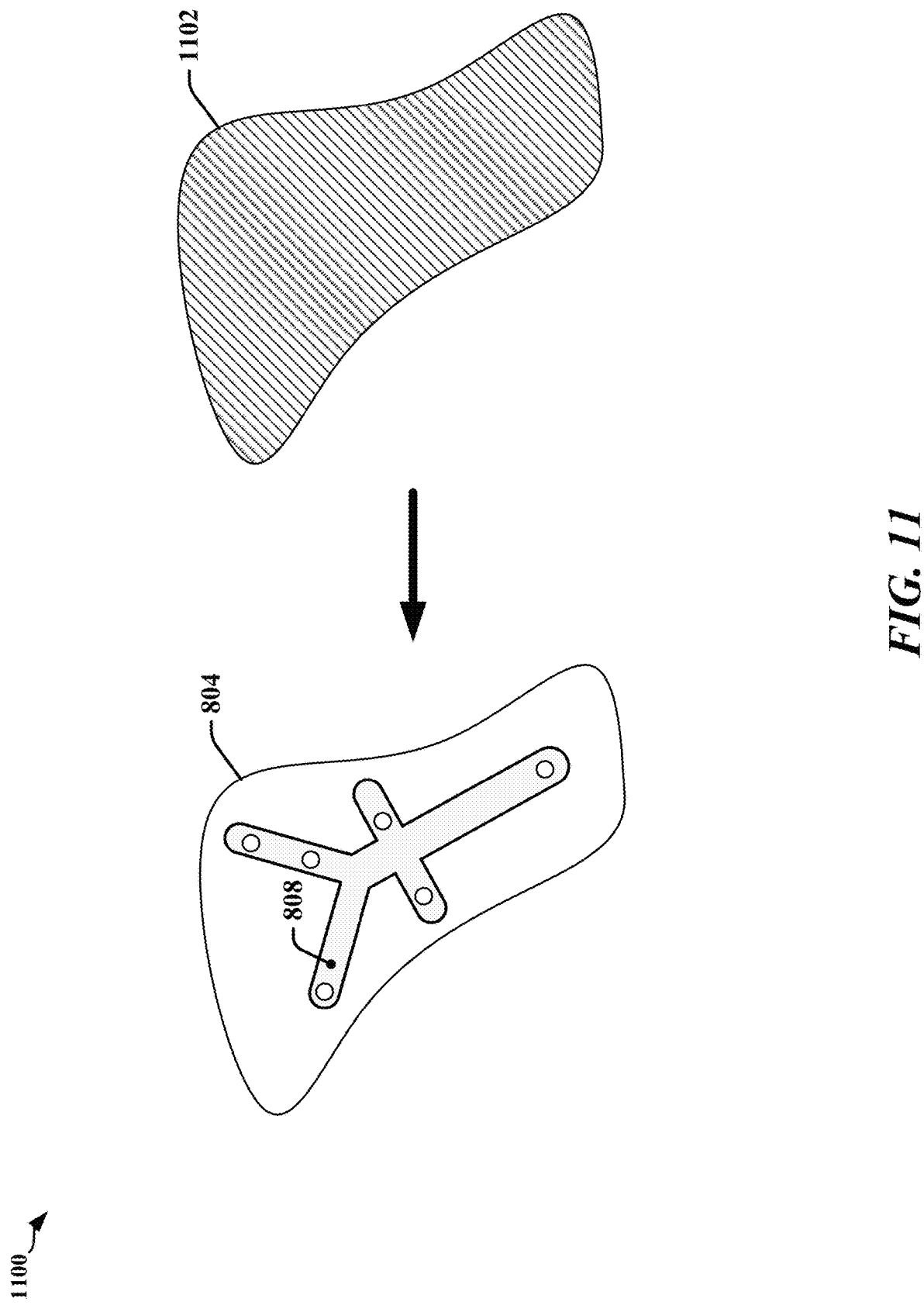
FIG. 11 illustrates a second example of a partially completed device conforming to the design of a simulated device provided in accordance with certain aspects disclosed herein.

FIG. 11 illustrates a second example of a partially-completed membrane 1100 conforming to the design of the simulated membrane 604. The first layer 804 has been joined to the reinforcement binder 808. The second layer 1102 has been cut and can be joined or attached to the first layer 804.

Figure 12:
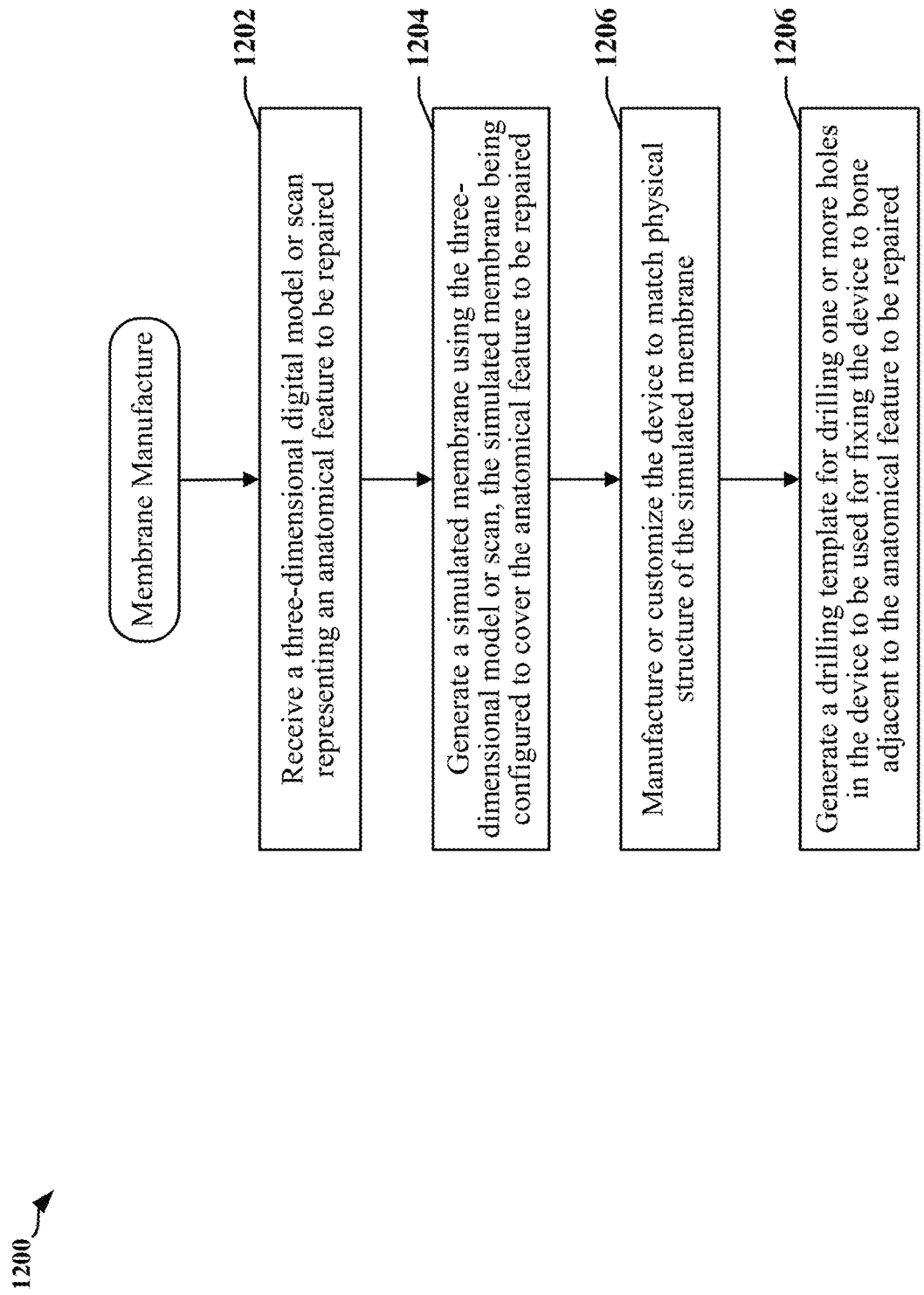
FIG. 12 illustrates a first example of a method for guiding bone and tissue regeneration for a bone defect with a device provided in accordance with certain aspects disclosed herein.

FIG. 12 is a flowchart 1200 illustrating a first example of a method for manufacturing a device used in a procedure for repairing a bone defect by bone and tissue regeneration. In some implementations, the device may include layers formed from collagen, polytetrafluoroethylene, and/or other materials. The operations of the method presented below are intended to be illustrative. In some implementations, the method may be accomplished with one or more additional operations not described, and/or without one or more of the operations discussed. Additionally, the order in which the operations of the method are illustrated in FIG. 12 and described herein is not intended to be limiting.

At block 1202, a three-dimensional model representing an anatomical feature to be repaired may be received at a manufacturing system. The three-dimensional model may be generated using a measuring system, a scanning system, an imaging system and/or a processing system. At block 1204, the manufacturing system or another apparatus may generate a simulated membrane using the three-dimensional model. The simulated membrane may be configured to cover a simulation or model of the anatomical feature to be repaired. At block 1206, the manufacturing system may manufacture or customize the device to match physical structure of the simulated membrane. At block 1208, the manufacturing system may generate a drilling template for drilling one or more holes in the device to be used for fixing the device to bone adjacent to the anatomical feature to be repaired. In some examples, the manufacturing system may drill the holes using the drilling template.

In one example, the manufacturing system may manufacture the device by producing a template corresponding to the simulated membrane, and then cutting a premanufactured membrane according to the template to obtain the device. In another example, the manufacturing system may manufacture the device by printing at least one layer of material using template information derived from the simulated membrane and joining the at least one layer of material to one or more other layers of material to obtain the device. The manufacturing system may include a 3D printer in some instances that receives instructions, data or code that describes or represents the simulated membrane and that prints a physical membrane corresponding to the simulated membrane.

In one example, the manufacturing system may generate a digital or digitized two-dimensional flattened version of the simulated membrane, produce a trimming guide that includes an opening corresponding to the flattened version of the simulated membrane, and use the trimming guide to trim a premanufactured membrane. The trimming guide may be produced by a 3D printer or mill. The manufacturing system may be configured to select the premanufactured membrane from a catalog of membranes based on fit to size and shape of the flattened version of the simulated membrane, provide a cut-out in the trimming guide, and mark or cut the premanufactured membrane through the opening while the premanufactured membrane is held in the cut-out. The cut-out may be configured to hold the premanufactured membrane. The premanufactured membrane may be applied to the anatomical feature to be repaired after the premanufactured membrane is trimmed. The premanufactured membrane adopts a three-dimensional shape corresponding to the shape of the simulated membrane when the premanufactured membrane is applied to the anatomical feature to be repaired.

In some implementations, the manufacturing system may produce a device, or constituent components of a device that includes a first layer configured to contact bone, the first layer comprising ePTFE, and a second layer comprising high density, cell occlusive PTFE configured to substantially prevent fibrous connective tissue from growing into the bone defect. The device may comprise at least one layer having collagen, bioresorbable polymer, animal tissue, or human tissue.

In one example, the device has a size, a density, or a spacing defined by the simulated membrane and that is calculated by a modeling system based on one or more characteristics of a material included in the finished device, a thickness of the finished device, or a size of the finished device.

In certain implementations, a reinforcement binder is configured to attach the device to the bone adjacent to the anatomical feature to be repaired. The reinforcement binder may include a plurality of elongated members extending from a junction, including a first elongated member having a free end that extends away from the junction. The reinforcement binder may include a hole formed in the first elongated member, the hole configured to receive a fastener that passes through a first layer of the device and a second layer of the device and that holds the device in place at the bone defect. The fastener may comprise a pin, tack, suture, or screw. The reinforcement binder may be deployed between the first layer of the device and the second layer of the device. The reinforcement binder may be constructed from titanium. The one or more holes in the device may be drilled using a drilling template generated using the three-dimensional model.

In some instances, the membrane may be manufactured by producing a template corresponding to the simulation, and cutting a premanufactured membrane according to the template to obtain the membrane. Manufacturing the membrane may include printing one or more layers of material using information derived from the simulation, and joining the one or more layers of material to obtain the membrane.

A device manufactured in accordance with certain aspects of this disclosure and configured for repair of a bone defect comprises a first layer configured to contact bone, the first layer comprising ePTFE, a second layer comprising high density, cell occlusive PTFE configured to substantially prevent fibrous connective tissue from growing into the bone defect, and one or more holes drilled through the device and configured to receive fasteners for fixing the device to bone adjacent to the anatomical feature to be repaired. The device may be manufactured using template information generated from a three-dimensional model representing an anatomical feature to be repaired.

In one implementation, the device is manufactured by cutting a premanufactured membrane according to the template information. In certain implementations, the device is manufactured using one or more layers of material printed using the template information. Layers may be printed using a 3D printer. Layers of material, including printed layers may be joined to obtain the device.

In some examples, the device comprises at least one layer having collagen, bioresorbable polymer, animal tissue, or human tissue. The device may include a combination of materials configured with a size, a density, or a spacing defined by the template information, where the template information may be based on one or more characteristics of a material included in the finished device, a thickness of the finished device, or a size of the finished device.

In some examples, the device may include a reinforcement binder configured to couple the device with the bone adjacent to the anatomical feature to be repaired. The reinforcement binder may comprise a plurality of elongated members extending from a junction, including a first elongated member having a free end that extends away from the junction, and a hole formed in the first elongated member, the hole configured to receive a fastener that passes through a first layer of the device and a second layer of the device and that holds the device in place at the bone defect. In various examples, the fastener comprises a pin, tack, suture, or screw. In some examples, the reinforcement binder is deployed between the first layer of the device and the second layer of the device.

Figure 13:
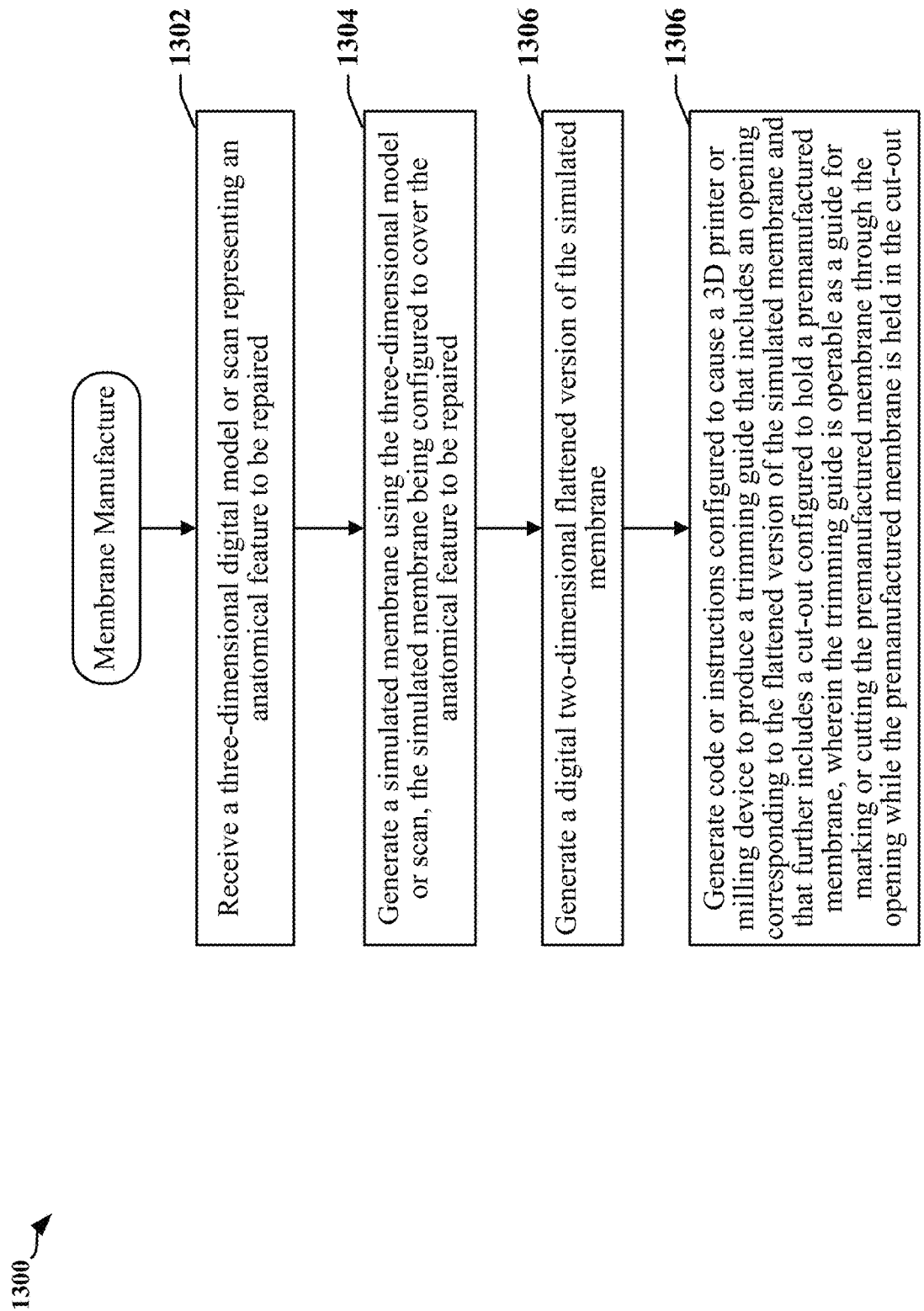
FIG. 13 illustrates a second example of a method for guiding bone and tissue regeneration for a bone defect with a device provided in accordance with certain aspects disclosed herein.

FIG. 13 is a flowchart 1300 illustrating a second example of a method for manufacturing a device used in a procedure for repairing a bone defect by bone and tissue regeneration. In this example, a trimming guide is printed and used to cut or trim a premanufactured membrane. The premanufactured membrane may be commercially available and may be selected from a catalog or other listing. In some implementations, the device may include layers formed from collagen, polytetrafluoroethylene, and/or other materials. The operations of the method presented below are intended to be illustrative. In some implementations, the method may be accomplished with one or more additional operations not described, and/or without one or more of the operations discussed. Additionally, the order in which the operations of the method are illustrated in FIG. 13 and described herein is not intended to be limiting.

At block 1302, a 3D digital model or scan is received, where the 3D digital model or scan represents, inter alia, an anatomical feature to be repaired. At block 1304, a simulated membrane may be generated using the three-dimensional model, the simulated membrane being configured to cover the anatomical feature to be repaired. At block 1306, a digital two-dimensional flattened version of the simulated membrane may be generated. At block 1308, code or instructions may be generated and configured to cause a 3D printer or milling device to produce a trimming guide that includes an opening corresponding to the flattened version of the simulated membrane and that further includes a cut-out configured to hold a premanufactured membrane. The trimming guide may be operative as a guide for marking or cutting the premanufactured membrane through the opening while the premanufactured membrane is held in the cut-out.

In some examples, a drilling template may be generated for drilling one or more holes in the premanufactured membrane after trimming. The holes may be arranged or configured to fix the device to bone adjacent to the anatomical feature to be repaired. The premanufactured membrane may be selected from a catalog of membranes based on fit to size and shape of the flattened version of the simulated membrane. The modeling system may include a listing of available membranes and associated specifications and may select a membrane for trimming based on fit. Best fit may be determined based on overall dimensions of the membrane, dimensions of a reinforcement binder, constituent materials and other reasons. The three-dimensional model may be generated using a measuring system, a scanning system, an imaging system and/or a processing system. the manufacturing system or another apparatus may generate the simulated membrane using the three-dimensional model, the simulated membrane being configured to cover the anatomical feature to be repaired.

Figure 14:
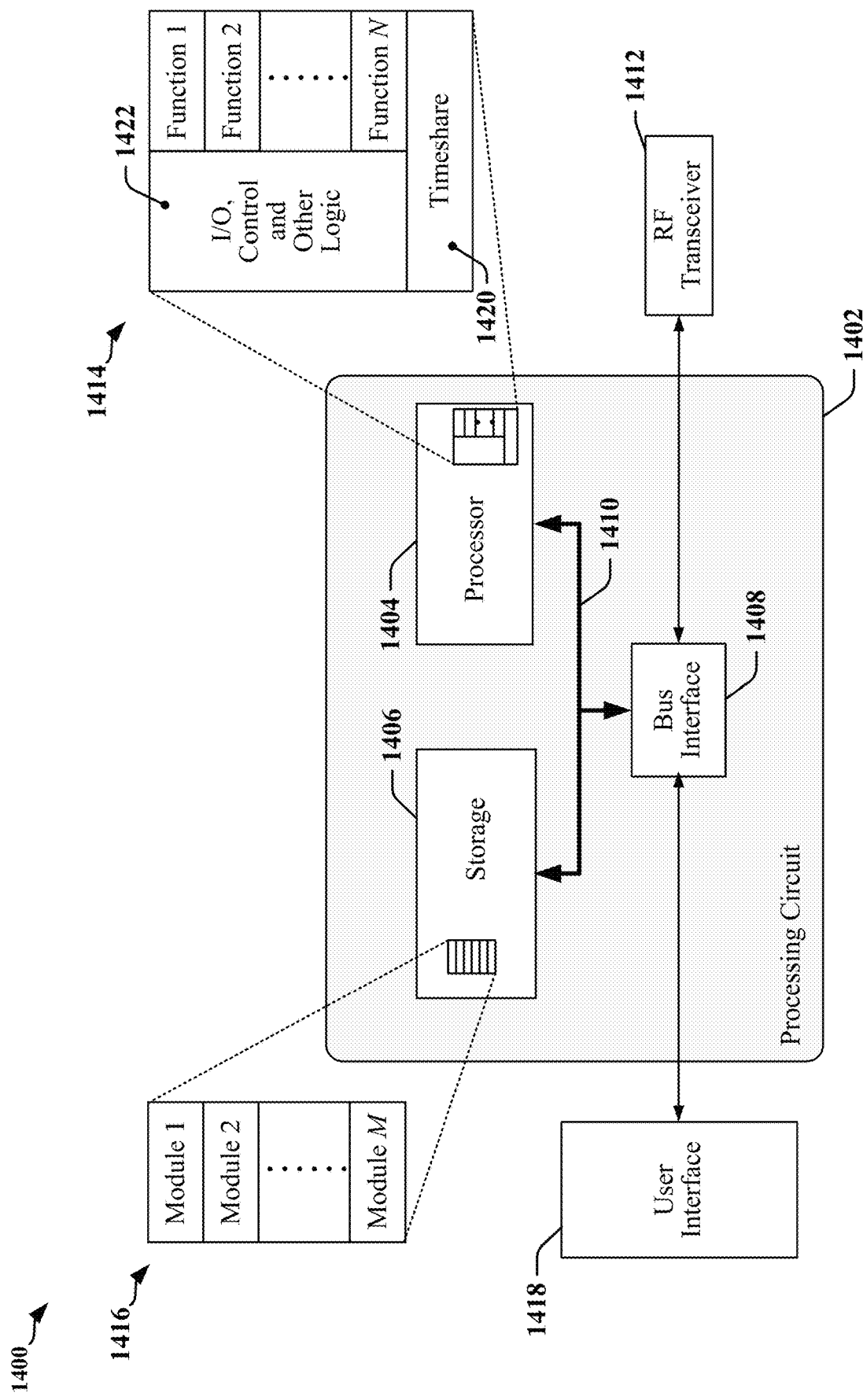
FIG. 14 is a diagram illustrating an example of an apparatus employing a processing circuit that may be adapted according to certain aspects disclosed herein.

FIG. 14 is a conceptual diagram illustrating a simplified example of a hardware implementation for an apparatus 1400 employing a processing circuit 1402 that may be configured to perform one or more functions disclosed herein. For example, the apparatus 1400 may comprise or be implemented in a manufacturing system and the processing circuit 1402 may be configured to control certain operations or processes associated with the manufacturing system. In accordance with various aspects of the disclosure, an element, or any portion of an element, or any combination of elements as disclosed herein may be implemented using the processing circuit 1402. The processing circuit 1402 may include one or more processors 1404 that are controlled by some combination of hardware and software modules. Examples of processors 1404 include microprocessors, microcontrollers, digital signal processors (DSPs), ASICs field programmable gate arrays (FPGAs), programmable logic devices (PLDs), state machines, sequencers, gated logic, discrete hardware circuits, and other suitable hardware configured to perform the various functionality described throughout this disclosure. The one or more processors 1404 may include specialized processors that perform specific functions, and that may be configured, augmented or controlled by one of the software modules 1416. The one or more processors 1404 may be configured through a combination of software modules 1416 loaded during initialization, and further configured by loading or unloading one or more software modules 1416 during operation.

In the illustrated example, the processing circuit 1402 may be implemented with a bus architecture, represented generally by the bus 1410. The bus 1410 may include any number of interconnecting buses and bridges depending on the specific application of the processing circuit 1402 and the overall design constraints. The bus 1410 links together various circuits including the one or more processors 1404, and storage media 1406. Storage media 1406 may include memory devices and mass storage devices and may be referred to herein as computer-readable media and/or processor-readable media. The bus 1410 may also link various other circuits such as timing sources, timers, peripherals, voltage regulators, and power management circuits. A bus interface 1408 may provide an interface between the bus 1410 and one or more line interface circuits 1412. A line interface circuit 1412 may be provided for each networking technology supported by the processing circuit. In some instances, multiple networking technologies may share some or all of the circuitry or processing modules found in a line interface circuit 1412. Each line interface circuit 1412 provides a means for communicating with various other apparatus over a transmission medium. Depending upon the nature of the apparatus 1400, a user interface 1418 (e.g., keypad, display, speaker, microphone, joystick) may also be provided, and may be communicatively coupled to the bus 1410 directly or through the bus interface 1408.

A processor 1404 may be responsible for managing the bus 1410 and for general processing that may include the execution of software stored in a computer-readable medium that may include the storage media 1406. In this respect, the processing circuit 1402, including the processor 1404, may be used to implement any of the methods, functions and techniques disclosed herein. The storage media 1406 may be used for storing data that is manipulated by the processor 1404 when executing software, and the software may be configured to implement any one of the methods disclosed herein.

One or more processors 1404 in the processing circuit 1402 may execute software. Software shall be construed broadly to mean instructions, instruction sets, code, code segments, program code, programs, subprograms, software modules, applications, software applications, software packages, routines, subroutines, objects, executables, threads of execution, procedures, functions, algorithms, etc., whether referred to as software, firmware, middleware, microcode, hardware description language, or otherwise. The software may reside in computer-readable form in the storage media 1406 or in external computer readable storage medium. The external computer-readable storage medium may include a non-transitory computer-readable storage medium. A non-transitory computer-readable storage medium includes, by way of example, a magnetic storage device (e.g., hard disk, floppy disk, magnetic strip), an optical disk (e.g., a compact disc (CD) or a digital versatile disc (DVD)), a smart card, a flash memory device (e.g., a "flash drive," a card, a stick, or a key drive), a random access memory (RAM), a read only memory (ROM), a programmable ROM (PROM), an erasable PROM (EPROM), an electrically erasable PROM (EEPROM), a register, a removable disk, and any other suitable medium for storing software and/or instructions that may be accessed and read by a computer. The computer-readable storage medium and/or other storage media 1406 may also include, by way of example, a carrier wave, a transmission line, and any other suitable medium for transmitting software and/or instructions that may be accessed and read by a computer. Computer-readable storage medium and/or the storage media 1406 may reside in the processing circuit 1402, in the processor 1404, external to the processing circuit 1402, or be distributed across multiple entities including the processing circuit 1402. The computer-readable storage medium and/or other storage media 1406 may be embodied in a computer program product. By way of example, a computer program product may include a computer-readable medium in packaging materials. Those skilled in the art will recognize how best to implement the described functionality presented throughout this disclosure depending on the particular application and the overall design constraints imposed on the overall system.

The storage media 1406 may maintain software maintained and/or organized in loadable code segments, modules, applications, programs, etc., which may be referred to herein as software modules 1416. Each of the software modules 1416 may include instructions and data that, when installed or loaded on the processing circuit 1402 and executed by the one or more processors 1404, contribute to a run-time image 1414 that controls the operation of the one or more processors 1404. When executed, certain instructions may cause the processing circuit 1402 to perform functions in accordance with certain methods, algorithms and processes described herein.

Some of the software modules 1416 may be loaded during initialization of the processing circuit 1402, and these software modules 1416 may configure the processing circuit 1402 to enable performance of the various functions disclosed herein. For example, some software modules 1416 may configure internal devices and/or logic circuits 1422 of the processor 1404, and may manage access to external devices such as the line interface circuit 1412, the bus interface 1408, the user interface 1418, timers, mathematical coprocessors, and so on. The software modules 1416 may include a control program and/or an operating system that interacts with interrupt handlers and device drivers, and that controls access to various resources provided by the processing circuit 1402. The resources may include memory, processing time, access to the line interface circuit 1412, the user interface 1418, and so on.

One or more processors 1404 of the processing circuit 1402 may be multifunctional, whereby some of the software modules 1416 are loaded and configured to perform different functions or different instances of the same function. The one or more processors 1404 may additionally be adapted to manage background tasks initiated in response to inputs from the user interface 1418, the line interface circuit 1412, and device drivers, for example. To support the performance of multiple functions, the one or more processors 1404 may be configured to provide a multitasking environment, whereby each of a plurality of functions is implemented as a set of tasks serviced by the one or more processors 1404 as needed or desired. In one example, the multitasking environment may be implemented using a timesharing program 1420 that passes control of a processor 1404 between different tasks, whereby each task returns control of the one or more processors 1404 to the timesharing program 1420 upon completion of any outstanding operations and/or in response to an input such as an interrupt. When a task has control of the one or more processors 1404, the processing circuit is effectively specialized for the purposes addressed by the function associated with the controlling task. The timesharing program 1420 may include an operating system, a main loop that transfers control on a round-robin basis, a function that allocates control of the one or more processors 1404 in accordance with a prioritization of the functions, and/or an interrupt driven main loop that responds to external events by providing control of the one or more processors 1404 to a handling function.

In one implementation, the storage media 1406 provides a non-transitory processor-readable storage medium configured with code that, when executed, causes the processing circuit 1402 to receive or generate a three-dimensional model or scan representing an anatomical feature to be repaired may be received at a manufacturing system. The three-dimensional model may be generated using a measuring system, a scanning system, an imaging system and/or a processing system. The code may cause the processing circuit 1402 to generate a simulated membrane using the three-dimensional model or scan, the simulated membrane being configured to cover the anatomical feature to be repaired. The code may cause the processing circuit 1402 to manufacture the device to match physical structure of the simulated membrane. The code may cause the processing circuit 1402 to generate a drilling template for drilling one or more holes in the device to be used for fixing the device to bone adjacent to the anatomical feature to be repaired. In some examples, a manufacturing system may drill the holes using a drilling template generated from the three-dimensional model.

The code may cause the processing circuit 1402 to generate a digital two-dimensional flattened version of the simulated membrane, produce a 3D printed or milled trimming guide that includes an opening corresponding to the flattened version of the simulated membrane. The code may cause the processing circuit 1402 to use the trimming guide to trim a premanufactured membrane. The code may cause the processing circuit 1402 to select the premanufactured membrane from a catalog of membranes based on fit to size and shape of the flattened version of the simulated membrane, provide a cut-out in the trimming guide, the cut-out being configured to hold the premanufactured membrane. The premanufactured membrane may be cut or marked through the opening while the premanufactured membrane is held in the cut-out.

In one example, the manufacturing system may manufacture the device by producing a template corresponding to the simulated membrane, and then cutting a premanufactured membrane according to the template to obtain the device. In another example, the manufacturing system may manufacture the device by printing at least one layer of material using template information derived from the simulated membrane and joining the at least one layer of material to one or more other layers of material to obtain the device. The manufacturing system may include a 3D printer in some instances.

In one example, the manufacturing system may generate a two-dimensional flattened version of the simulated membrane, produce a trimming guide that includes an opening corresponding to the flattened version of the simulated membrane, and use the trimming guide to trim a premanufactured membrane. The manufacturing system may select the premanufactured membrane from a catalog of membranes based on fit to size and shape of the flattened version of the simulated membrane, provide a cut-out in the trimming guide, and mark or cut the premanufactured membrane through the opening while the premanufactured membrane is held in the cut-out. The cut-out may be configured to hold the premanufactured membrane.

In some examples, the manufacturing system may produce a device, or constituent components of a device that includes a first layer configured to contact bone, the first layer comprising ePTFE, and a second layer comprising high density, cell occlusive PTFE configured to substantially prevent fibrous connective tissue from growing into the bone defect. The device may comprise at least one layer having collagen, bioresorbable polymer, animal tissue, or human tissue.

In one example, the device has a size, a density, or a spacing defined by the simulated membrane and that is calculated by a modeling system based on one or more characteristics of a material included in the finished device, a thickness of the finished device, or a size of the finished device.

In certain examples, a reinforcement binder is configured to attach the device to the bone adjacent to the anatomical feature to be repaired. The reinforcement binder may include a plurality of elongated members extending from a junction, including a first elongated member having a free end that extends away from the junction. The reinforcement binder may include a hole formed in the first elongated member, the hole configured to receive a fastener that passes through a first layer of the device and a second layer of the device and that holds the device in place at the bone defect. The fastener may comprise a pin, tack, suture, or screw. The reinforcement binder may be deployed between the first layer of the device and the second layer of the device. The reinforcement binder may be constructed from titanium. The one or more holes in the device may be drilled using a drilling template generated using the three-dimensional model.

In some instances, the membrane may be manufactured by producing a template corresponding to the simulation, and cutting a premanufactured membrane according to the template to obtain the membrane. Manufacturing the membrane may include printing one or more layers of material using information derived from the simulation, and joining the one or more layers of material to obtain the membrane.

In another implementation, the storage media 1406 is configured with code that, when executed, causes the processing circuit 1402 to receive a three-dimensional representation simulating an anatomical feature to be repaired, produce one or more templates and/or control code that can be used to control or enable manufacture of the membrane to match physical structure of the simulation, and produce one or more templates and/or control code that can be used to control machinery that drills one or more holes in the membrane to be used for fixing the membrane to bone adjacent to the anatomical feature to be repaired. The three-dimensional representation may include a simulation of a membrane configured to cover the anatomical feature to be repaired.

The membrane may have a first layer configured to contact bone, the first layer including ePTFE, and a second layer including high density, cell occlusive PTFE configured to substantially prevent fibrous connective tissue from growing into the bone defect. The membrane may include at least one layer having collagen, bioresorbable polymer, animal tissue, or human tissue. A size, density, or spacing defined by the simulation may be calculated by a modeling system based on one or more characteristics of a material included in the membrane, a thickness of the membrane, or a size of the membrane.

The membrane may include a reinforcement binder configured to couple the membrane with the bone adjacent to the anatomical feature to be repaired. The reinforcement binder may have a plurality of elongated members extending from a junction, including a first elongated member having a free end that extends away from the junction. The reinforcement binder may have a hole formed in the first elongated member, the hole configured to receive a fastener that passes through a first layer of the membrane and a second layer of the membrane and that holds the membrane in place at the bone defect. The fastener may be a pin, tack, suture, or screw. The reinforcement binder may be deployed between the first layer and the second layer of the membrane. The reinforcement binder may be a titanium reinforcement binder.

The processor-readable storage medium may be configured with code that causes the processing circuit 1402 to produce a template corresponding to the simulation, and may provide instructions that causes a cutting machine to cut a premanufactured membrane according to the template to obtain the membrane. The processor-readable storage medium may be configured with code that causes the processing circuit 1402 to print one or more layers of material using information derived from the simulation, and cause the one or more layers of material to be joined, thereby obtaining the membrane.

In another implementation, the storage media 1406 is configured with code that, when executed, causes the processing circuit 1402 to receive a three-dimensional digital model or scan representing an anatomical feature to be repaired, generate a simulated membrane using the 3D model, and generate a digital two-dimensional (2D) flattened version of the simulated membrane. The simulated membrane may be configured to cover the anatomical feature to be repaired. The processor-readable storage medium may be configured with code that causes the processing circuit 1402 to generate code or instructions configured to cause a 3D printer or milling device to produce a trimming guide that includes an opening corresponding to the flattened version of the simulated membrane and that further includes a cut-out configured to hold a premanufactured membrane. The trimming guide may be used as a guide for marking or cutting the premanufactured membrane through the opening while the premanufactured membrane is held in the cut-out. The processor-readable storage medium may be configured with code that causes the processing circuit 1402 to generate a drilling template for drilling one or more holes in the premanufactured membrane after trimming, the holes being configured to fix the device to bone adjacent to the anatomical feature to be repaired. The processor-readable storage medium may be configured with code that causes the processing circuit 1402 to select the premanufactured membrane from a catalog of membranes based on fit to size and shape of the flattened version of the simulated membrane. The processor-readable storage medium may be configured with code that causes the processing circuit 1402 to receive a three-dimensional digital model or scan representing an anatomical feature to be repaired.

Although the systems and methods of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

The invention claimed is:

1. A method for manufacturing a device configured to guide bone and tissue regeneration, comprising:
   receiving a three-dimensional digital model or scan representing an anatomical feature that includes a defect to be repaired;
   modifying the three-dimensional digital model in a manner that simulates the effect of adding a packing material to the defect;
   generating a simulated membrane using the three-dimensional model or scan, the simulated membrane being configured to cover the anatomical feature to be repaired and to cover the packing material;
   manufacturing the device to match physical structure of the simulated membrane; and
   generating a drilling template for drilling one or more holes in the device to be used for fixing the device to bone adjacent to the anatomical feature to be repaired.

2. The method of claim 1, wherein modifying the three-dimensional digital model comprises:
   mimicking characteristics and attributes of granular particles of autogenous bone, allograft, xenograft or bioresorbable hydroxyapatite.

3. The method of claim 1, further comprising:
   generating a digital two-dimensional flattened version of the simulated membrane;
   producing a 3D printed or milled trimming guide that includes an opening corresponding to the flattened version of the simulated membrane; and
   using the trimming guide to trim a premanufactured membrane.

4. The method of claim 3, further comprising:
   selecting the premanufactured membrane from a catalog of membranes based on fit to size and shape of the flattened version of the simulated membrane;
   providing a cut-out in the trimming guide, wherein the cut-out is configured to hold the premanufactured membrane; and
   marking or cutting the premanufactured membrane through the opening while the premanufactured membrane is held in the cut-out.

5. The method of claim 1, wherein manufacturing the device comprises:
   embossing the device with a pattern selected based on type, size and composition of the packing material.

6. The method of claim 1, wherein manufacturing the device comprises:
   printing or cutting at least one layer of material using template information derived from the simulated membrane; and
   joining the at least one layer of material to one or more other layers of material to obtain the device.

7. The method of claim 1, wherein the device comprises a first layer configured to contact bone, the first layer comprising expanded polytetrafluoroethylene (ePTFE) and a second layer comprising high density, cell occlusive polytetrafluoroethylene (PTFE) configured to substantially prevent fibrous connective tissue from growing into a bone defect.

8. The method of claim 1, wherein the device comprises at least one layer having collagen, bioresorbable polymer, animal tissue, or human tissue.

9. The method of claim 1, wherein one or more of a size, a density, or a spacing defined by the simulated membrane is configured to cause the device to exert a maximum or minimum pressure on the packing material added to the defect.

10. The method of claim 1, further comprising:
attaching the device to the bone adjacent to the anatomical feature to be repaired using a reinforcement binder.

11. The method of claim 10, wherein the reinforcement binder comprises:
a plurality of elongated members extending from a junction, including a first elongated member having a free end that extends away from the junction; and
a hole formed in the first elongated member, the hole configured to receive a fastener that passes through a first layer of the device and a second layer of the device and that holds the device in place at a bone defect, wherein the fastener comprises a pin, tack, suture, or screw.

12. The method of claim 10, wherein the reinforcement binder is a titanium reinforcement binder and is deployed between a first layer of the device and a second layer of the device.

13. A processor-readable storage medium configured with code that, when executed by a processor, causes the processor to:
receive a three-dimensional digital model or scan representing an anatomical feature that includes a defect to be repaired;
modify the three-dimensional digital model in a manner that simulates the effect of adding a packing material to the defect;
generate a simulated membrane using the three-dimensional model, the simulated membrane being configured to cover the anatomical feature to be repaired and to cover the packing material;
generate a digital two-dimensional flattened version of the simulated membrane; and
generate code or instructions configured to cause a three-dimensional printer (3D printer) or milling device to produce a trimming guide that includes an opening corresponding to the flattened version of the simulated membrane and that further includes a cut-out configured to hold a premanufactured membrane,
wherein the trimming guide is operable as a guide for marking or cutting the premanufactured membrane through the opening while the premanufactured membrane is held in the cut-out.

14. The processor-readable storage medium of claim 13, further configured with code for causing the processor to:
generate a drilling template for drilling one or more holes in the premanufactured membrane after trimming, the holes being configured to fix the device to bone adjacent to the anatomical feature to be repaired.

15. The processor-readable storage medium of claim 13, further configured with code for causing the processor to:
select the premanufactured membrane from a catalog of membranes based on fit to size and shape of the flattened version of the simulated membrane.

16. The processor-readable storage medium of claim 13, further configured with code for causing the processor to:
mimic characteristics and attributes of the packing material.

17. The processor-readable storage medium of claim 16, wherein the packing material comprises granular particles of autogenous bone, allograft, xenograft or bioresorbable hydroxyapatite.

18. The processor-readable storage medium of claim 13, further configured with code for causing the processor to:
emboss at least one surface of the device with a pattern selected based on type, size and composition of the packing material.

19. The processor-readable storage medium of claim 13, further configured with code for causing the processor to:
print or cut a plurality of layers from one or more materials using template information derived from the simulated membrane; and
join the plurality of layers to obtain the device.

20. The processor-readable storage medium of claim 13, wherein the device comprises a first layer configured to contact bone, the first layer comprising expanded polytetrafluoroethylene (ePTFE) and a second layer comprising high density, cell occlusive polytetrafluoroethylene (PTFE) configured to substantially prevent fibrous connective tissue from growing into a bone defect.

21. The processor-readable storage medium of claim 13, wherein the device comprises at least one layer having collagen, bioresorbable polymer, animal tissue, or human tissue.

22. The processor-readable storage medium of claim 13, further configured with code for causing the processor to:
dimension the simulated membrane is configured to cause the device to exert a maximum or minimum pressure on the packing material added to the defect.

23. The processor-readable storage medium of claim 13, further configured with code for causing the processor to:
attach the device to bone adjacent to the anatomical feature to be repaired using a reinforcement binder.

24. The processor-readable storage medium of claim 23, wherein the reinforcement binder comprises:
a plurality of elongated members extending from a junction, including a first elongated member having a free end that extends away from the junction; and
a hole formed in the first elongated member, the hole configured to receive a fastener that passes through a first layer of the device and a second layer of the device and that holds the device in place at a bone defect, wherein the fastener comprises a pin, tack, suture, or screw.

25. The processor-readable storage medium of claim 23, wherein the reinforcement binder is a titanium reinforcement binder and is deployed between a first layer of the device and a second layer of the device.

* * * * *